(12) United States Patent
Deckmyn et al.

(10) Patent No.: US 7,332,162 B1
(45) Date of Patent: Feb. 19, 2008

(54) CELL LINES, LIGANDS AND ANTIBODY FRAGMENTS FOR USE IN PHARMACEUTICAL COMPOSITIONS FOR PREVENTING AND TREATING HAEMOSTASIS DISORDERS

(75) Inventors: Hans Deckmyn, Linden (BE); Nancy Cauwenberghs, Londerzeel (BE)

(73) Assignee: K.U. Leuven Research & Development, Leuven (BE)

( * ) Notice: Subject to any disclaimer, the term of this patent is extended or adjusted under 35 U.S.C. 154(b) by 718 days.

(21) Appl. No.: 10/049,868

(22) PCT Filed: Aug. 8, 2000

(86) PCT No.: PCT/EP00/07874

§ 371 (c)(1),
(2), (4) Date: Jun. 4, 2002

(87) PCT Pub. No.: WO01/10911

PCT Pub. Date: Aug. 8, 2000

(30) Foreign Application Priority Data

Aug. 10, 1999 (GB) .................................. 9918788.2
Feb. 2, 2000 (EP) .................................. 00102032

(51) Int. Cl.
*A61K 39/395* (2006.01)
*C07K 16/28* (2006.01)

(52) U.S. Cl. .............................. 424/133.1; 424/143.1; 530/388.22

(58) Field of Classification Search ............. 530/387.3, 530/388.25; 424/133.1, 145.1
See application file for complete search history.

(56) References Cited

U.S. PATENT DOCUMENTS

| 4,731,245 | A | * | 3/1988 | Tsurumizu et al. |
| 5,336,667 | A | | 8/1994 | Kirby |
| 5,455,030 | A | * | 10/1995 | Ladner et al. |
| 5,486,361 | A | | 1/1996 | Gralnick |
| 5,958,765 | A | * | 9/1999 | Brams et al. ............... 435/339 |
| 6,998,469 | B2 | * | 2/2006 | Tandon et al. ......... 530/388.25 |
| 7,112,661 | B1 | * | 9/2006 | Miller ...................... 530/387.1 |

FOREIGN PATENT DOCUMENTS

WO    PCT/US99/25495     5/2000
WO    WO-00/26667 A1     5/2000

OTHER PUBLICATIONS

Tandon et al Interaction of human platelets with laminin and identification of the 67 kDa laminin receptor on platelets. Biochem J. Mar. 1, 1991;274 (Pt 2):535-42.*
Asch et al ., Identification and isolation of a platelet GPIb-like protein in human umbilical vein endothelial cells and bovine aortic smooth muscle cells. J Clin Invest. May 1988;81(5):1600-7.*
Wicki et al. Eur J Biochem. Structure and function of platelet membrane glycoproteins Ib and V. Effects of leukocyte elastase and other proteases on platelets response to von Willebrand factor and thrombin. Nov. 15, 1985;153(1):1-11.*
Rudikoff S et al., Single amino acid substitution altering antigen-binding specificity. Proc Natl Sci U S A. 79(6):1979-1983 1982.*
Panka et al. Variable region framework differences result in decreased or increased affinity of variant anti-digoxin antibodies. Proc Natl Acad Sci U S A. 85(9):3080-3084, 1988.*
Owens RJ, Young RJ. The genetic engineering of monoclonal antibodies. J Immunol Methods. 168(2):149-165, 1994.*
Miller JL et al. Isolation and Characterization of Single Chain Human Antibodies Directed Against Epitopes within Human Platelet GPIbα, Nov. 15, 1998, blood 92(10), Abstract.*
Reverter, "Inhibition of Platelet—mediated, Tissue Factor induced . . .", J. Clin. Invest, vol. a8, No. 3, Aug. 1996, pp. 863-874.
Pareti, "Interaction of porcine von Willebrand factor with the platelet . . . ", British J. of Haematology, vol. 82, 1992, pp. 81-86.
Becker, "Effects of an Antiplatlet Glycoprotein Ib Antibody on . . . ", Blood, vol. 74, No. 2, Aug. 1, 1989, pp. 690-694.
Ward, "Epitope and functional characterization of the CD42 . . . ", Platlet antigens, pp. 1336-1337.
Cowenberghs, "Antithrombotic Effect of Platelet Glycoprotein Ib-Blocking . . . ", Arteriosclerosis, Thrombosis abd Vascular Biology.
Coller, "A Murine Monoclonal Antibody that Completely Blocks . . . ", J. Clin. Invest. vol. 72, Jul. 1983, pp. 325-338.
Shetler, "Antithrombotic Assessment of the Effects of Combination . . . ", 1996, American Heart Association, pp. 1719-1725.
Simoons, "Randomized Trial of a GPIIb/IIIa Platelet Receptor . . . ", Circulation, vol. 89, No. 2, Feb. 1994, pp. 596-603.
Schultz, "Use of C7E3 Fab in Conjunction With Primary Coronary . . . ", Catherization and Coardiovascular Diagnosis, vol. 39, 1996, pp. 143-148.
Lincoff, "Platelet Glycoprotein IIb/IIIa Receptor Blocade And . . . ", New England J. of Med., vol. 336, No. 24, Jun. 12, 1997, pp. 1689-1697.
Gold, "PharmacodynamicStudy of F (ab)2 Fragments of . . . ", J. Clin. Invest., vol. 86, Aug. 1990, pp. 651-659, 1990.
Bergmeler et al., "Structural and Functional Characterization of the Mouse Von Willebrand Factor Receptor GPIb-IX with Novel Monoclonal Antibodies", *Blood*, 95:886-893 (2000).
Cadroy et al., "Relative Antithrombotic Effects of Monoclonal Antibodies Targeting Different Platelet Glycoprotein-Adhesive Molecule Interactions in Nonhuman Primates", *Blood*, 83:3218-3224 (1994).
Kulkarni et al., "A Revised Model of Platelet Aggregation," *J Clin Invest*. 105:783-791 (2000).
Ravanat et al., "Differential effects of monoclonal antibodies to rat GPIIb-IIIa, GPIbα, or GPV on platelet function and in vivo survival," *Thromb Haemost*. 82:528 (1999).

* cited by examiner

*Primary Examiner*—Maher M. Haddad
(74) *Attorney, Agent, or Firm*—Clark & Elbing LLP

(57) ABSTRACT

A ligand derived from, e.g. a Fab fragment of, a monoclonal antibody obtainable from the cell line deposited with the Belgian Coordinated Collections of Micro-organisms under accession number LMBP 5108CB binds to the human platelet glycoprotein GPib and prevents the binding of von Willebrand factor to said GPIb without inducing thrombocytopenia. The said ligand is useful, in admixture with a pharmaceutically acceptable carrier, in a pharmaceutical composition, optionally further comprising a thrombolytic agent, for preventing and/or treating haemostasis disorders.

7 Claims, 11 Drawing Sheets

FIGURE 1
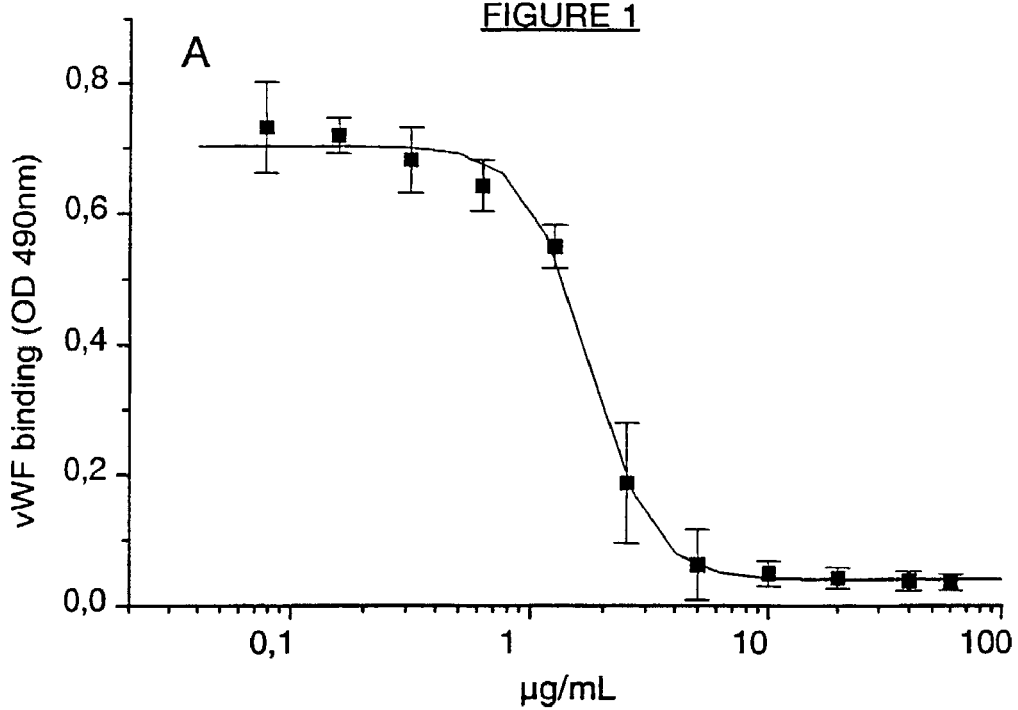
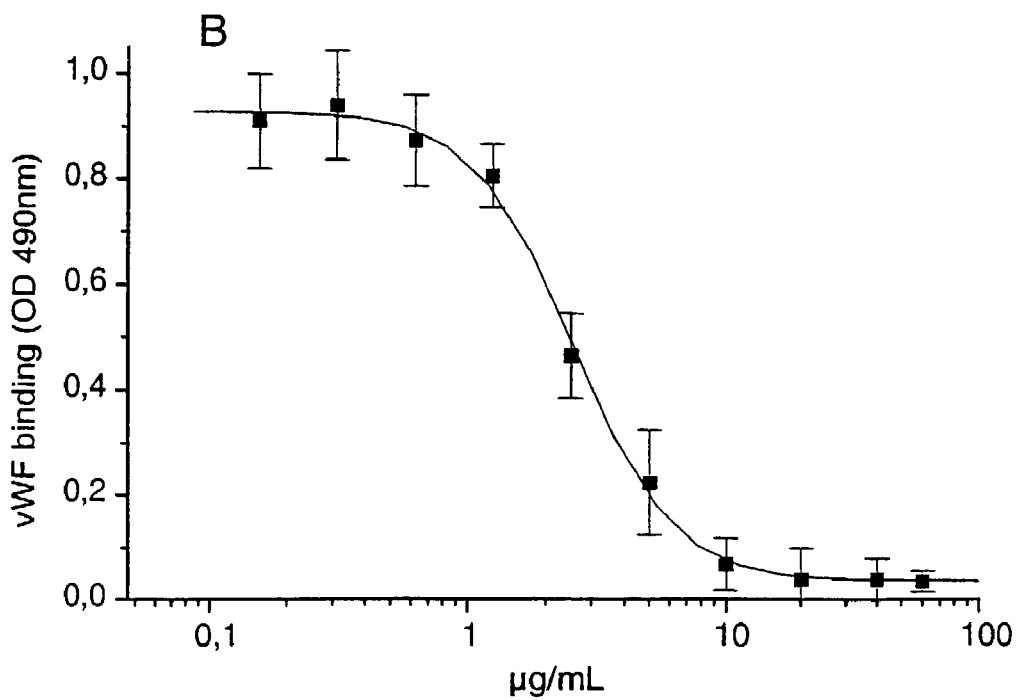

FIGURE 5
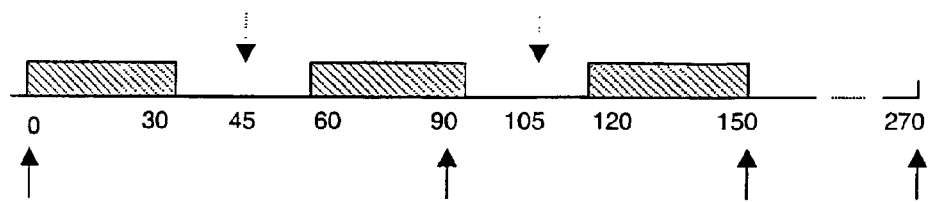
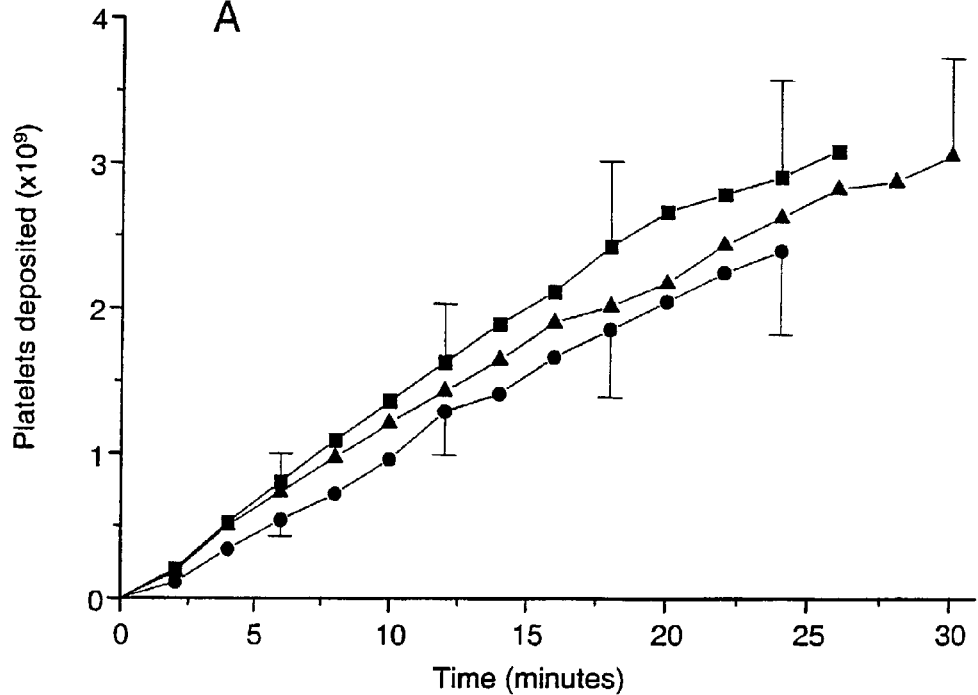
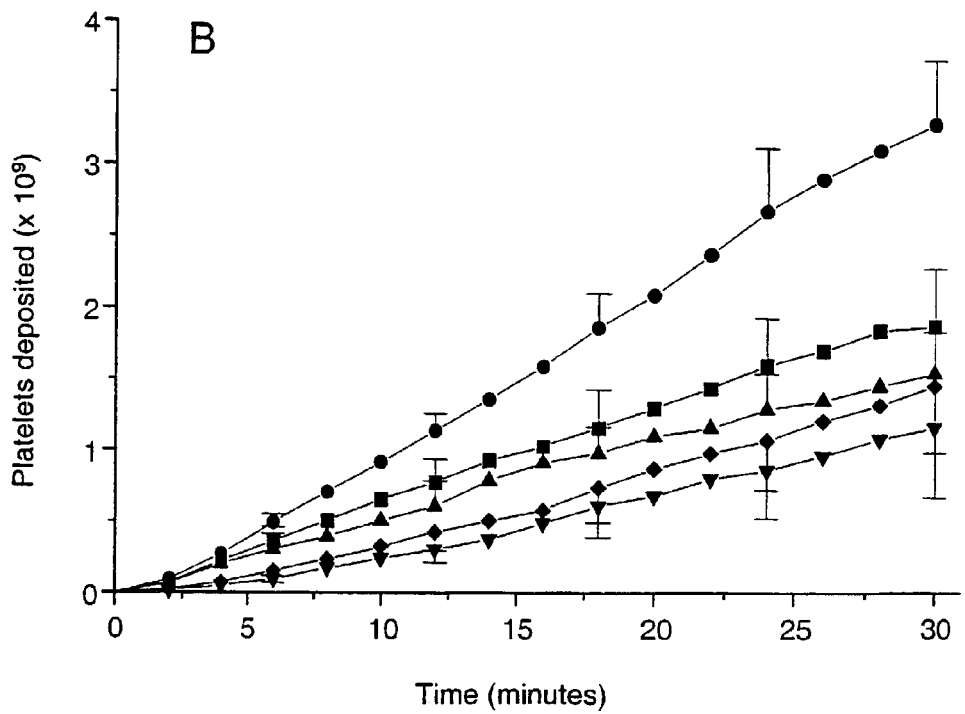

FIGURE 7
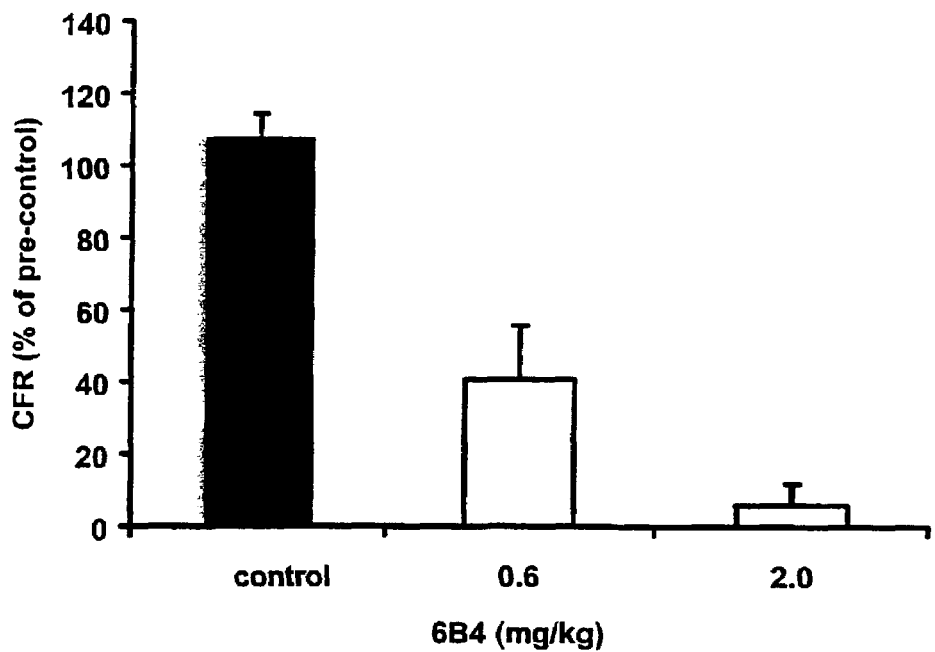
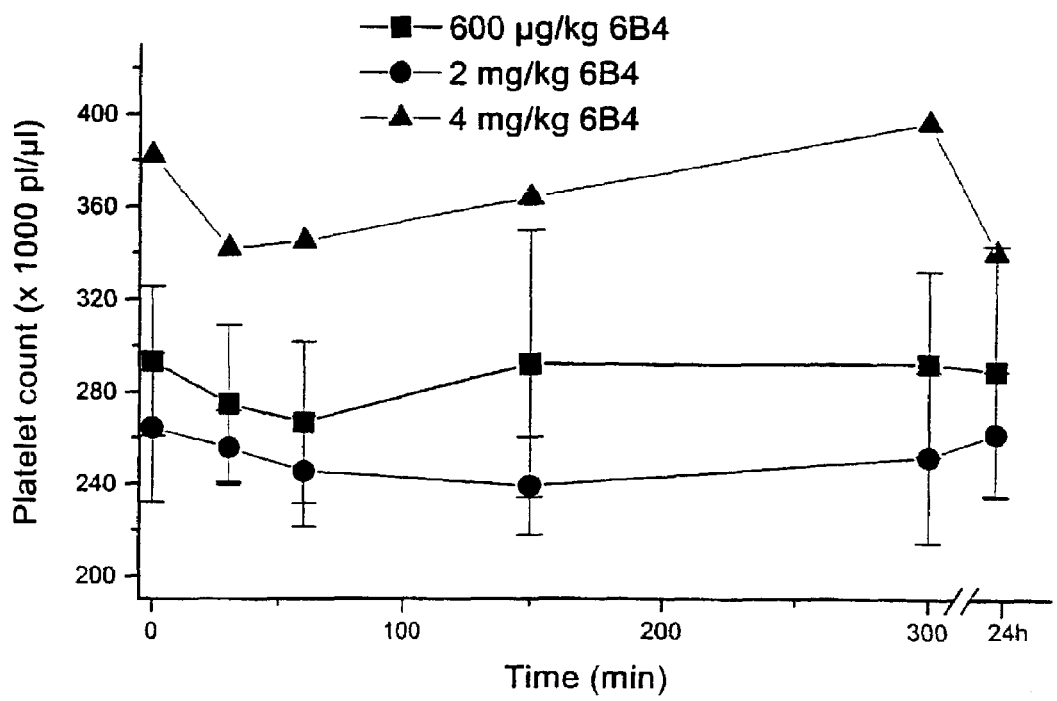
FIGURE 8

FIGURE 9
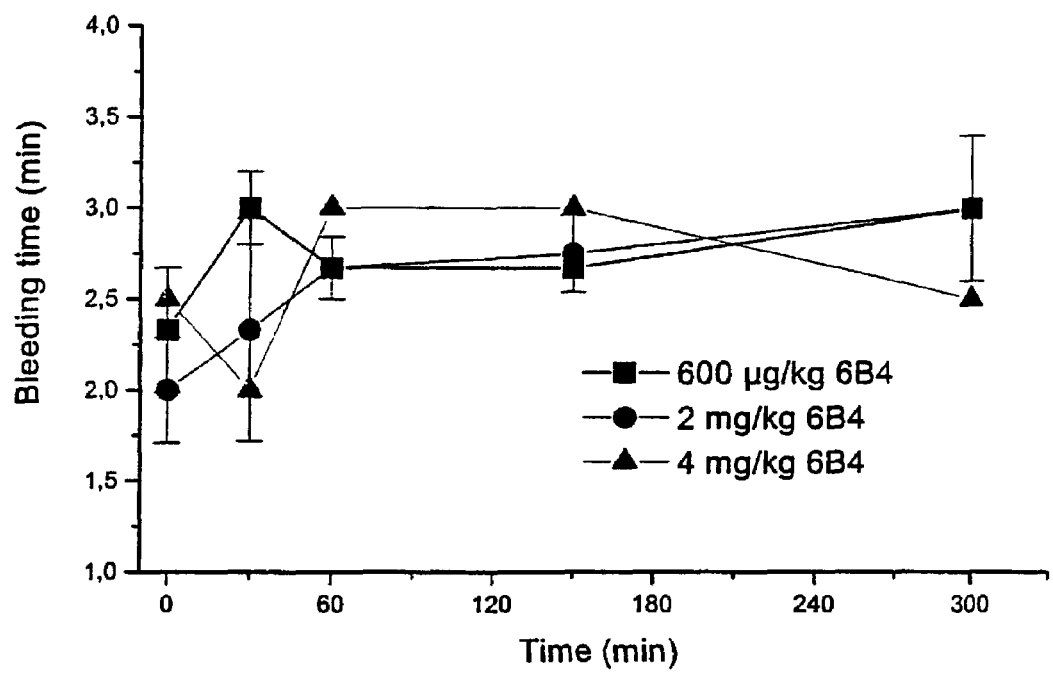
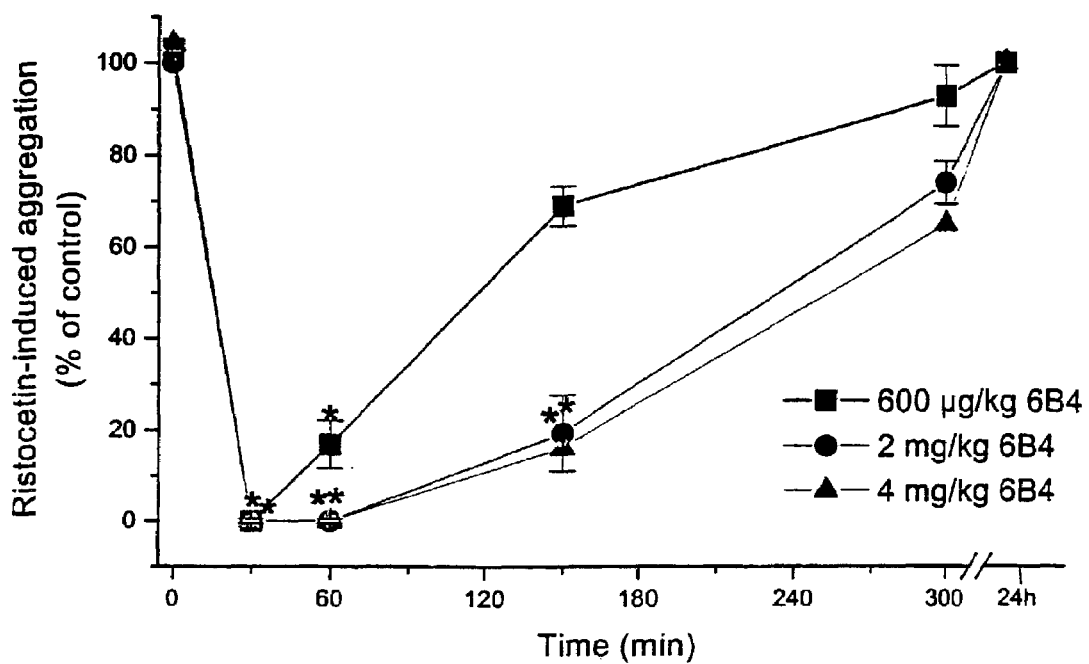
FIGURE 10

FIGURE 12

Nucleic Acid Sequence of 6B4VL

```
    Vκback primer
┌─────────────────────────┐
│GACATTGAGCTCACCCAGTCTCCA│GCAATCATGTCTGCATCTCCAGGGGAGAAGGTCACC      60
 D  I  E  L  T  Q  S  P   A  I  M  S  A  S  P  G  E  K  V  T       20

ATGACCTGCAGTGCCAGTTCAAGTGTTAATTACATGCACTGGTTCCAGCAGGAGTCGGGC      120
 M  T  C  S  A  S  S  S  V  N  Y  M  H  W  F  Q  Q  E  S  G        40
          ─────────────────────────
                   CDR1

ACCTTCCCCAAAAGAAGGATTTATGACACATCCAAACTGGCTTCTGGAGTCCCTGCTCGC      180
 T  F  P  K  R  R  I  Y  D  T  S  K  L  A  S  G  V  P  A  R        60
                         ──────────────────────
                                  CDR2

CTCAGTGGCAGTGGGTCTGGGACAGAATTCACCCTGGAAATCAGTAGAGTGAAGGCTGAG      240
 L  S  G  S  G  S  G  T  E  F  T  L  E  I  S  R  V  K  A  E        80

GATGTGGGTGTGTATTACTGTCAACAACTTGTAGAGTATCCGCTCACGTTCGGTGCTGGG      300
 D  V  G  V  Y  Y  C  Q  Q  L  V  E  Y  P  L  T  F  G  A  G       100
                    ──────────────────────
                             CDR3    Vκ2for primer
                                    ┌──────────────────────────
ACCAAGCTGGAGCTGAAACGGGCTGAT│GCTGCACCAACTGTATCCATCTTCAAGCTTCC      359
 T  K  L  E  L  K  R  A  D  A  A  P  T  V  S  I  F  K  L         119
```

FIGURE 13

Nucleic Acid Sequence of 6B4VH

```
        V_H back primer
┌─────────────────────────────┐
│CAGGTGCAGCTGCAGGAGTCTGGA│CCTGGCCTGGTGGCGCCCTCACAGAGCCTGTCCATC      60
 Q   V   Q   L   Q   E   S   G   P   G   L   V   A   P   S   Q   S   L   S   I      20

ACTTGCACTGTCTCTGGGATTTCATTAAACAGATATGGTGTACACTGGGTTCGCCAGCCT                       120
 T   C   T   V   S   G   I   S   L   N   R   Y   G   V   H   W   V   R   Q   P      40
                                    ─────────────────────
                                           CDR1

CCAGGAAAGGGTCTGGAGTGGCTGGGAGTAATATGGACTGGTGGAAGCACAAATTATAAT                       180
 P   G   K   G   L   E   W   L   G   V   I   W   T   G   G   S   T   N   Y   N      60
                                        ───────────────────────────
                                                    CDR2

TCGGCTCTCATGTCCAGACTGAGCATCAGCAAAGACAACTCCAAGAGCCAAGTTTTCTTA                       240
 S   A   L   M   S   R   L   S   I   S   K   D   N   S   K   S   Q   V   F   L      80
─────

AAAATGAACAGTCTGCAGACTGATGACACAGCCATGTACTACTGTGCCAGAGATCGATCT                       300
 K   M   N   S   L   Q   T   D   D   T   A   M   Y   Y   C   A   R   D   R   S      100
                                                            ─────────────
                                                    V_H for primer
ACTATGATTACGGCCTATGCTATGGACTAC│TGGGGCCAAGGGACCACGGTCACCGTCTCC                      360
                              └──────────────────────────────
 T   M   I   T   A   Y   A   M   D   Y   W   G   Q   G   T   T   V   T   V   S      120
 ──────────────────────────
           CDR3
┌───┐
│TCA│   363
└───┘
 S       120
```

CELL LINES, LIGANDS AND ANTIBODY FRAGMENTS FOR USE IN PHARMACEUTICAL COMPOSITIONS FOR PREVENTING AND TREATING HAEMOSTASIS DISORDERS

The present invention relates to novel cell lines and to ligands, namely human and/or humanized monoclonal antibodies, as well as fragments such as Fab or single variable domains and derivatives and combinations thereof, obtainable from the said cell line. It also relates to pharmaceutical compositions comprising said ligands or antibody fragments and to methods of preventing and treating haemostasis disorders, in particular antithrombotic treatments in humans, by administration of the said ligands or antibody fragments to patients in need thereof. It further relates to a polynucleotide encoding for the antigen-binding Fab fragment of a monoclonal antibody derivable from the said cell line.

BACKGROUND OF THE INVENTION

The coagulation of blood involves a cascading series of reactions leading to the formation of fibrin. The coagulation cascade consists of two overlapping pathways required for hemostasis. The intrinsic pathway comprises protein factors present in circulating blood, while the extrinsic pathway requires tissue factor which is expressed on the cell surface of a variety of tissues in response to vascular injury. Agents interfering with the coagulation cascade, such as heparin and coumarin derivatives, have well known therapeutic uses in the prophylaxis of venous thrombosis.

Aspirin also provides a protective effect against thrombosis. It induces a long-lasting functional defect in platelets, detectable clinically as a prolongation of the bleeding time, through inhibition of the cyclooxygenase activity of the human platelet enzyme prostaglandin H-synthase (PGHS-1) with doses as low as 30 to 75 mg. Since gastrointestinal side effects of aspirin appear to be dose-dependent, and for secondary prevention, treatment with aspirin is recommended for an indefinite period, there are practical reasons to choose the lowest effective dose. Further it has been speculated that a low dose (30 mg daily) might be more antithrombotic but attempts to identify the optimal dosage have yielded conflicting results. It has been claimed that the dose of aspirin needed to suppress fully platelet aggregation may be higher in patients with cerebrovascular disease than in healthy subjects and may vary from time to time in the same patient. However, aspirin in any daily dose of 30 mg or higher reduces the risk of major vascular events by 20% at most, which leaves much room for improvement. Further, the inhibiting role of aspirin may lead to prevention of thrombosis and to excess bleeding. The balance between the two depends critically on the absolute thrombotic versus hemorrhage risk of the patient.

In patients with acute myocardial infarction, reduction of infarct size, preservation of ventricular function and reduction in mortality has been demonstrated with various thrombolytic agents. However these agents still have significant shortcomings, including the need for large therapeutic doses, limited fibrin specificity, and significant associated bleeding tendency. Recombinant tissue plasminogen activator (t-PA) restores complete patency in just over one half of patients, whereas streptokinase achieves this goal in less than one third. Further, reocclusion after thrombolytic therapy occurs in 5 to 10% of cases during the hospital stay and in up to 30% within the first year according to Verheugt et al., *J. Am. Coll. Cardiol.* (1996) 27:618-627. Numerous studies have examined the effects of adjunctive antithrombin therapy for patients with acute myocardial infarction. For instance, U.S. Pat. No. 5,589,173 discloses a method for dissolving and preventing reformation of an occluding thrombus comprising administering a tissue factor protein antagonist, such as a monoclonal or polyclonal antibody, in adjunction to a thrombolytic agent.

In arterial blood flow, the platelet adhesion is mainly supported by the platelet receptor glycoprotein (GP) 1b which interacts with von Willebrand factor (vWF) at the site of vessel wall injury. Blood platelets, through the processes of adhesion, activation, shape change, release reaction and aggregation, form the first line of defence when blood vessels are damaged. They form a hemostatic plug at the site of injury to prevent excessive blood loss. Extensive platelet activation however may overcome the normal thromboregulatory mechanisms that limit the size of the hemostatic plug. Platelets then become major prothrombotic offenders predisposing to vaso-occlusive disease.

The formation of a platelet plug during primary haemostasis and of an occluding thrombus in arterial thrombosis involves common pathways. The first event is platelet adhesion to subendothelial collagen, exposed upon vessel injury, which can be a ruptured atherosclerotic plaque. Circulating vWF binds to the collagen and, under the influence of high shear stress, undergoes a conformational change allowing it to bind to its receptor, GPIb/IX/V, on the platelet membrane. This interaction is essential in order to produce a thrombus, at least in smaller vessels or stenosed arteries where shear stress is high, and results in slowing down the progress of the platelets across the damaged surface. Full immobilisation of platelets occurs when collagen binds to its receptor GPIa/IIa (integrin $\alpha_2\beta_1$). In addition, collagen activates platelets mainly by binding to GPVI, another collagen receptor. When platelets are activated, GPIIb/IIIa (integrin $\alpha_{IIb}\beta_3$) undergoes a conformational change and acquires the ability to bind to fibrinogen and vWF which crosslink adjacent platelets to finally form platelet aggregates.

Lately much effort has been directed to develop antibodies and peptides that can block the binding of the adhesive proteins to GPIIb/IIIa and many of these are being tested in clinical trials. One approach to blocking platelet aggregation involves monoclonal antibodies specific for GPIIb/IIIa receptors. Specifically, a murine monoclonal antibody named 7 E3 useful in the treatment of human thrombotic diseases is described in EP-A-206,532 and U.S. Pat. No. 5,387,413. However it is known in the art that murine antibodies have characteristics which may severely limit their use in human therapy. As foreign proteins, they may elicit an anti-immunoglobulin response termed human anti-mouse antibody (HAMA) that reduces or destroys their therapeutic efficacy and/or provokes allergic or hypersensitivity reactions in patients, as taught by Jaffers et al., *Transplantation* (1986) 41:572. The need for re-administration in therapies of thromboembolic disorders increases the likelihood of such immune reactions. While the use of human monoclonal antibodies would address this limitation, it has proven difficult to generate large amounts of such antibodies by conventional hybridoma technology.

Recombinant technology has therefore been used to construct "humanized" antibodies that maintain the high binding affinity of murine monoclonal antibodies but exhibit reduced immunogenicity in humans. In particular, there have been suggested chimeric antibodies in which the variable region (V) of a non-human antibody is combined with the constant (C) region of a human antibody. As an example, the murine Fc fragment was removed from 7E3 and replaced by the human constant immunoglobulin G region to form a chimera known as c7E3 Fab or abciximab. Obtention of such chimeric immunoglobulins is described in detail in U.S. Pat. No. 5,770,198.

The potential for synergism between GPIIb/IIIa inhibition by monoclonal antibody 7E3 Fab and thrombolytic therapy was evaluated by Kleiman et al., *J. Am. Coll. Cardiol* (1993) 22:381-389. Major bleeding was frequent in this study. Hence, the potential for life-threatening bleeding is clearly a major concern with this combination of powerful antithrombotic compounds.

The GPIb-vWF axis therefore presents an attractive alternative to GPIIb/IIIa-fibrinogen as a target for platelet inhibition, since a suitable inhibitor might be expected to down regulate other manifestations of platelet activity such as granule release, thought to play a role in the development of arteriosclerosis. Activation of platelets is accompanied by secretion of vasoactive substances (thromboxane A2, serotonin) as well as growth factors such as PGDF. Therefore, early inhibition of platelet activation and hence prevention of the secretion of their growth and migration factors, via a GPIb blocker, would reduce the proliferation of smooth muscle cells and restenosis after thrombolytic therapy. Moreover, the interaction of GPIb with the damaged vessel wall (adhesion, as well as aggregation and secretion of platelet content) is highly blood flow dependent. Unlike GPIIb/IIIa interactions, GPIb-vWF interaction occurs exclusively under the high flow conditions, as occurs in small arteries or created by arterial stenoses. Hence, GPIb inhibition represents theoretically an ideal way to target effective platelet inhibition to damaged arterial areas. GPIb inhibition therefore appears particularly suited to treat patients with acute coronary syndromes, transient cerebral attacks and claudication due to peripheral arterial diseases, including prevention of the frequently letal thrombotic complications of acute coronary syndromes, angioplasty, unstable angina and myocardial infarction.

Despite these potential advantages, the development of compounds that interfere with the vWF-GPIb axis has lagged behind. Only a few in vivo studies described the effects of inhibition of platelet adhesion on thrombogenesis. They include the use of anti-vWF monodonal antibodies, GPIb binding snake venom proteins like echicetin and crotalin, aurin tricarboxylic acid that binds to vWF and recombinant vWF fragments like VCL, all of which inhibit vWF-GPIb interaction. All these molecules were anti-thrombotic, particularly in studies where a thrombus was formed under high shear conditions. U.S. Pat. No. 5,486,361 discloses a monoclonal antibody 4H12 which specifically binds to the α chain of GPIb and, by means of this interaction, totally inhibits the binding of thrombin to normal human platelets. In addition, it inhibits more than 90% of thrombin-induced von Willebrand factor or fibrinogen binding to platelets. Further, 4H12 does not inhibit ristocetin- or botrocetin-induced binding of von Willebrand factor to platelet cells, which indicates that this antibody does not prevent von Willebrand factor binding to GPIb. A number of potent inhibitory anti-GPIb antibodies, such as LJIb1 disclosed by F. Pareti et al. in British Journal of Haematology (1992) 82, 81-86, have been produced and were extensively tested with respect to their in vitro effect under both static (platelet agglutination, vWF-binding) and flow conditions. However for none of these anti-human GPIb antibodies an in vivo anti-thrombotic effect could be demonstrated. In vivo data obtained by B. Becker and J. L. Miller (Blood (1989)2:680-694) describe the effect of injecting guinea pigs with intact antibody or F(ab')$_2$ fragments of PG1, a monoclonal anti-guinea pig GPIb antibody. After intraperitoneal injection of the intact antibody, a hemorrhagic state was produced with a significant lengthening of the bleeding time and drop of the platelet count to 50% of its baseline value. Injection of 0.53 to 2.5 mg/kg of the F(ab')$_2$ fragments did not decrease the platelet count more than 21%, and bleeding times never increased by more than one minute over baseline values. However, in this particular study the antithrombotic effect of the F(ab')$_2$ fragments was not further investigated by e.g. testing the fragments in an animal thrombosis model. In a follow-up study J. L. Miller et al., Arterioscier. Thromb. (1991) 11:1231-6 disclosed that the F(ab')$_2$ fragments of PG1 in guinea pigs using these could effectively reduce thrombus formation on a laser-induced injury. Unfortunately, this antibody does not cmss react with human platelets and therefore it has no further clinical relevance for human therapy.

Part of this rather surprising lack of in vivo studies is due to the low cross reactivity of the anti-human GPIb monoclonal antibodies with platelets from commonly used laboratory animals. This predisposes to the use of non-human primates as experimental animals. However, even then attempts to perform in vivo studies are hampered because injection of the anti-GPIb monoclonal antibodies, as well as the snake venom protein echicetin that reacts with GPIb, invariably causes severe thrombocytopenia, as taught by US-A-5,336,667. WO-A-002667 further discloses monoclonal antibodies F$_{ab}$ fragments but does not discuss thrombocytopenia and does not mention in vivo tests.

One persistent concern with all available thrombolytic and anti-thrombotc agents, including aspirin, is to induce a risk of overdose and therefore of excessive and life-threatening bleeding. Therefore a first goal of the present invention is to provide a thrombus formation protective means by providing a platelet adhesion inhibitor that does not induce a risk of bleeding. A second goal of the present invention is to provide a thrombus formation protective means by providing an inhibitor of platelet adhesion without incurring the risk of thrombocytopenia, A third goal of the present invention is the targetting of platelet adhesion, activation and aggregation under high shear conditions, which is of particular importance in the setting of highly stenotic atherosclerotic lesions. The specific targetting of highly stenotic areas in the circulation should make GPIb inhibition particularly suitable for treating unstable angina and in the chronic prevention of arterial occlusion. Unlike with GPIIb/IIIa inhibition, platelet aggregation as well as hemostasis is not expected to be inhibited in low shear vessels, i.e. in veins and normal arteries. Bleeding complications from these vessels by inhibition of GPIb may therefore be expected to be better reduced than with GPIIb/IIIa inhibition.

SUMMARY OF THE INVENTION

The essence of this invention is that by using a ligand such as a monovalent Fab fragment of a certain inhibitory human GPIb antibody, a marked prevention of platelet dependent thrombus formation targetted to high shear flow vessels and without incurring thrombocytopenia can be obtained. Moreover, this is so far the only anti-human GPIb monoclonal antibody for which the antithrombotic efficacy has been proven in vivo in an animal thrombosis model.

The present invention therefore first includes a cell-line deposited with the Belgian Coordinated Collections of Micro-organisms, under accession number LMBP 5108CB. Secondly the present invention includes a ligand which binds to the human platelet glycoprotein GPIb and prevents the binding of von Willebrand factor (vWF) to GPIb and which preferably does not produce thrombocytopenia when administered to a primate (in this invention, the word "primate" also relates to humans) at a dose of up to at least 4 mg/kg by bolus intravenous administration. In particular the present invention includes a ligand derived from a monoclonal antibody such as 6B4 obtainable from the said cell line. Thirdly the present invention relates to an antigen-binding Fab fragment, or a homolog or derivative of such fragment (including a humanized fragment which might be divalent, trivalent or tetravalent), which may be obtained by proteolytic digestion of the said monoclonal antibody by papain, using methods well known in the art. Fourthly the present invention includes pharmaceutical compositions comprising said ligands or fragments which are useful for preventing and treating haemostasis disorders, in particular for anti-thrombotic treatments, in humans. Finally the present invention includes polynucleotide sequences encoding for the above-mentioned monoclonal antibodies or Fab fragments thereof. It will be appreciated that a multitude of nucleotide sequences fall under the scope of the present invention as a result of the redundancy in the genetic code. The present invention also includes nucleic acid molecules comprising sequences which are complementary to the coding sequence of said polynucleotides and the use of such molecules as DNA probes for detecting the said polynucleotides.

The present invention is first based on the observation of the antithrombotic effect of human platelet glycoprotein GPIb blocking monoclonal antibody 6B4 Fab fragment derived from the cell line LMBP 5108CB in a baboon model of arterial thrombosis. Two in vivo models were used and described in this invention: the first model is an arterio-venous shunt model in which an extracorporeal loop is made between the femoral artery and the femoral vein. Within this loop a collagenic graft is incorporated and the platelet deposition onto this graft is measured, as shown in examples 7-8 and FIGS. 5-6. Baboons were either pre-treated with said Fab fragment to study the effect on platelet deposition on a thrombogenic device, or treated 6 minutes after placement of the thrombogenic device in order to investigate the effect on inter-platelet cohesion. In this first study, it was observed that blockade of GPIb had no effect on platelet deposition onto a fresh thrombus, whereas pre-treatment effectively reduced thrombus formation. The second model is a clinically even more relevant model mimicking platelet-mediated thrombotic occlusion as occuring in stenosed and intimally damaged coronary arteries in vivo. In this second model a stenosis is applied to a damaged femoral artery, and blood flow is measured. Due to platelet aggregate formation the stenotic area occludes but reopens due to embolisation, resulting in regular cyclic flow reductions as shown in example 9.

Secondly, the present invention is based on in vitro and in vivo studies of the antithrombotic efficacy of the monoclonal antibody, 6B4 (IgG1), raised against human platelet glycoprotein Ib. In vitro, 6B4 potently inhibits the binding of vWF to human GPIb both under static and flow conditions, as further illustrated by the following examples, and it also binds to baboon platelets. When 6B4 was injected into baboons, both the intact monoclonal antibody and its F(ab')$_2$ fragments caused immediate and severe thrombocytopenia, whereas Fab fragments of 6B4 did not. Furthermore, Fab fragments studied in the two baboon models effectively prevented platelet-dependent arterial thrombosis.

BRIEF DESCRIPTION OF THE DRAWINGS

FIG. 1 shows the inhibiting effect of 6B4 Fab fragments on the ristocetin- and botrocetin-induced binding of vWF to rGPIb.

FIG. 5 shows platelet adhesion and deposition onto three thrombogenic devices placed in baboons either untreated (FIG. 5A) or treated (FIG. 5B) with 6B4 Fab fragments.

FIG. 7 shows the effect of 6B4 Fab fragments on cyclic flow reductions.

FIG. 8 shows the effect of 6B4 Fab fragments on platelet count.

FIG. 9 shows the effect of 6B4 Fab fragments on bleeding time.

FIG. 10 shows the inhibition of ex vivo platelet aggregation by 6B4 Fab fragments.

FIG. 12 shows (lower lines) the amino acid sequence (SEQ.No.3) and (upper lines) the nucleotide sequence (SEQ.No.1) for the variable regions VL of the light chains of the 6B4 monoclonal antibody.

FIG. 13 shows (lower lines) the amino acid sequence (SEQ.No.4) and (upper lines) the nucleotide sequence (SEQ.No.2) for the variable regions VH of the heavy chains of the 6B4 monoclonal antibody.

DEFINITIONS

Figure 2:
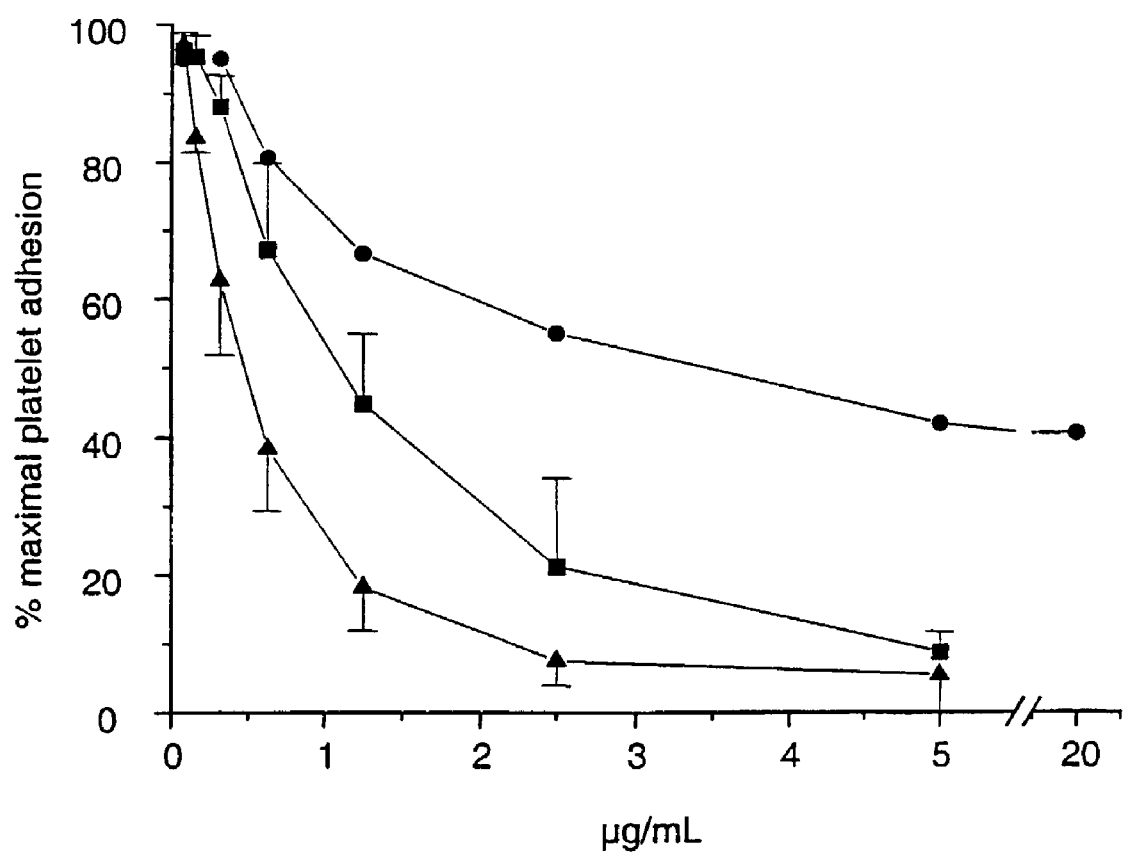
FIG. 2 shows the inhibiting effect of 6B4 Fab fragments on platelet adhesion to collagen type I under flow.

The term "antibody" refers to intact molecules as well as fragments thereof, which are capable of binding to the epitope determinant of the relevant factor or domain of the factor.

"Humanized antibody" as used herein, refers to antibody molecules in which amino acids have been replaced in the non-antigen binding regions in order to more closely resemble a human antibody.

The term "homolog" as used herein with reference to ligands in accordance with the present invention refers to a molecule which will compete with or inhibit binding of one of the ligands in accordance with the present invention to the target site. The binding should be specific, i.e. the binding of the alternative molecule should be as specific to the site as the ligand in accordance with the present invention. Where the ligands in accordance with the present invention include amino acid sequences, homology may include having at least about 60%, preferably at least 80%, more preferably at least 90% and most preferably at least 95% amino acid sequence identity with the relevant ligand.

DETAILED DESCRIPTION OF THE INVENTION

The present invention will be described with reference to certain embodiments and figures but the present invention is not limited thereto but only by the following claims.

The present invention provides a cell-line deposited with the Belgian Coordinated Collections of Micro-organisms, under accession number LMBP 5108CB. The present invention further provides cell lines producing monoclonal antibodies having a reactivity, namely a reactivity towards human GP Ib, substantially identical to that of monoclonal antibodies obtainable or obtained from cell line LMBP 5108CB, as well as the human monoclonal antibodies obtainable from the said further cell lines.

The present invention also provides ligands which are able to bind to the human platelet glycoprotein GPIb and also preferably able to prevent the binding of von Willebrand factor (vWF) to GPIb, in particular ligands derived from a monoclonal antibody (referred to as 6B4) obtainable from said cell line LMBP 5108CB or from equivalent cell lines such as above defined. More preferably, such a ligand should be able to recognize an epitope located on human platelet glycoprotein GPIb. For instance, the present invention relates to ligands of the above-mentioned type, being derived from a monoclonal antibody produced by on purpose immunization in animals. The present invention also provides an antigen-binding Fab fragment, or a homolog or derivative of such fragment, which may be obtained by proteolytic digestion of the said monoclonal antibody by papain, using methods well known in the art. In order to reduce the immunogenicity of the murine anti-GPIb monoclonal antibody 6B4, the present invention also includes the construction of a chimeric antibody, preferentially as a single-chain variable domain which combines the variable region of the mouse antibody with a human antibody constant region—a so-called humanized monoclonal antibody. The monoclonal antibodies produced in animals may be humanized, for instance by associating the binding complementarity determining region ("CDR") from the non-human monoclonal antibody with human framework regions—in particular the constant C region of human gene—such as disclosed by Jones et al. in *Nature* (1986) 321:522 or Riechmann in *Nature* (1988) 332:323, or otherwise hybridized.

This invention also provides using a ligand or a humanized or hybridized monoclonal antibody or an antigen-binding Fab fragment such as specified hereinbefore as a medicament. Although aspirin will continue to be widely used for patients with vascular disease, however there are a number of situations in which increased thrombotic risk requires the use of a more potent platelet inhibitor than aspirin. Conditions such as angioplasty, coronary stenting and thrombolysis are likely to require more potent platelet inhibitors. In these acute clinical situations, the fibrous cap over an atherosclerotic plaque has been ruptured which produces deep arterial injury and exposes a much more thrombogenic surface. Furthermore, high shear forces acting on platelets passing through severely narrowed stenoses can also overcome the inhibitory effects of aspirin. Therefore a GPIb antagonist according to the invention may be used for reducing the problems of occlusion and restenosis in patients undergoing angioplasty or for the prevention of reocclusion after succesful thrombolysis by tissue plasminogen activators, streptokinase or the like. It is believed that platelet activation, as a result of the platelet adhesion, is a key component in the failure of thrombolysis. Therefore a therapeutic approach towards blocking the GPIb-vWF interaction, that results in a down-regulation of platelet signalling, represents a new way of interfering in thrombus formation.

The present invention therefore further provides pharmaceutical compositions comprising a ligand or a humanized or hybridized monoclonal antibody or an antigen-binding Fab fragment such as specified hereinbefore, in admixture with a pharmaceutically acceptable carrier. More preferably the said pharmaceutical composition comprises a human or humanized or hybridized monoclonal antibody or an antigen-binding Fab fragment thereof obtainable from the cell line LMBP 5108CB. which are useful for preventing and treating haemostasis disorders, in particular for anti-thrombotic treatments, in humans.

The use of a GPIb blocker according to the present invention is believed to be more efficient in acute situations and, in some cases, as an adjunctive therapy together with other agents such as, among others, aspirin or heparin. The pharmaceutical composition of the present invention may therefore further comprise, in view of the so-called adjunctive therapy, a therapeutically effective amount of a thrombolytic agent. Such thrombolytic agents, as well as their usual dosage depending on the class to which they belong, are well known to those skilled in the art. Among numerous examples of thrombolytic agents which may be included in the pharmaceutical compositions of the invention, may be cited tissue plasminogen activators (t-Pa), streptokinase, reptilase, TNK-t-Pa or staphylokinase. The pharmaceutical composition should comprise the additional thrombolytic agent in a form which is suitable either for simultaneous use or for sequential use. Sequential, as used herein, means that the ligand or humanized monoclonal antibody or antigen-binding Fab fragment of the invention on the one hand and the known thrombolytic agent are administered to the patient in alternance but not within the same dosage unit.

Suitable pharmaceutical carriers for use in the pharmaceutical compositions of the invention are described for instance in Remington's Pharmaceutical Sciences $16^{th}$ ed. (1980) and their formulation is well known to those skilled in the art. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the monoclonal antibody or Fab fragment active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the monoclonal antibody active or Fab fragment ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition comprising the active ingredient may require protective coatings.

The pharmaceutical form suitable for injectionable use include sterile aqueous solutions or dispersions and sterile powders for the extemporaneous preparation thereof. Typical carriers therefore include biocompatible aqueous buffers, ethanol, glycerol, propylene glycol, polyethylene glycol and mixtures thereof.

The pharmaceutical composition and medicament in accordance with the present invention may be provided to a patient by means well known in the art. i.e. orally, intranasally, subcutaneously, intramuscularly, intradermally, intravenously, intraarterially, parenterally or by catheterization. For the reasons stated above, they will be especially useful for the treatment and/or prevention of disorders of haemostasis and particularly for antithrombotic treatment or prevention. Therefore the present invention further provides a method of treatment and/or prevention of such disorders by administering to a patient in need thereof a therapeutically effective amount of a ligand or a humanized monoclonal antibody or an antigen-binding Fab fragment such as specified hereinbefore, optionally together with (simultaneously or sequentially) a therapeutically effective amount of a thrombolytic agent such as above described.

The present invention also provides a polynucleotide sequence encoding for the antigen-binding Fab fragment, or homolog or derivative of the monoclonal antibody derived from cell line LMBP 5108CB. The present invention also provides nucleic acid molecules comprising a sequence which is complementary to the coding sequence of the said polynucleotide and the use of such molecules as DNA probes for detecting the said polynucleotide.

The present invention is further described by the following examples which are provided for illustration purposes only. Data were tested for statistically significant difference. Data given in the text are mean ± SE. P-values <0.05 are considered significantly different.

Example 1—preparation and purification of intact monoclonal antibody 6B4, F(ab')$_2$ and Fab fragments 6B4 (subtype IgG1), is a murine monoclonal antibody raised against purified human GPIb and obtainable from the cell line deposited with the Belgian Coordinated Collections of Micro-organisms under accession number LMBP 5108CB. When added at saturating concentrations, monoclonal antibody 6B4 totally abolishes both ristocetin- and botrocetin-induced human platelet aggregation as well as shear-induced platelet adhesion to human collagen type I tested in a Sakariassen-type flow chamber at $2600s^{-1}$.

Hybridoma cells producing the monoclonal antibody 6B4 were grown and subsequently injected into pristane (i.e. 2,6,10,14-tetramethyidecanoic acid)-primed Balb/c mice. After 10 days ascites fluid was collected. The immunoglobulin (IgG) was extracted from the ascites using protein-A-Sepharose CL-4B (available from Pharmacia, Roosendaal, Netherlands).

In order to prepare F(ab')$_2$ fragments, the monoclonal antibody 6B4 was dialyzed overnight against a 0.1 mol/I citrate buffer (pH 3.5) The antibody (200 parts) was digested by incubation with pepsin (1 part) available from Sigma (Saint-Louis, Mo.) for 1 hour at 37° C. Digestion was stopped by adding 1 volume of a 1M Tris HCl buffer (pH 9) to 10 volumes of antibody.

Monovalent Fab fragments were prepared by papain digestion as follows: a 1 volume of a 1M phosphate buffer (pH 7.3) was added to 10 volumes of the monoclonal antibody, then 1 volume papain (Sigma) was added to 25 volumes of the phosphate buffer containing monoclonal antibody, 10 mmol/I L-Cysteine HCl (Sigma) and 15 mmol/I ethylene diamine tetra acetic acid (hereinafter referred to as EDTA). After incubation for 3 hours at 37° C., digestion was stopped by adding a final concentration of 30 mmol/I freshly prepared iodoacetamide solution (Sigma), keeping the mixture in the dark at room temperature for 30 minutes.

Both F(ab')$_2$ and Fab fragments were further purified from contaminating intact IgG and Fc fragments using protein-A-Sepharose. The purified fragments were finally dialyzed against phosphate-buffered saline (hereinafter referred as PBS). Purity of the fragments was determined by sodium dodecylsulphate polyacrylamide gel electrophoresis and the protein concentration was measured using the bicinchonicic acid Protein Assay Reagent A (Pierce, Rockford, Ill.).

Example 2—Method for determining deposition of platelets

Autologous blood platelets were labelled with $^{111}$In-tropolone and imaging and quantification of the deposition of $^{111}$In-platelets were done as described by Kotze et al., J.Nucl.Med. (1991) 32:62-66. Briefly, image acquisition of the grafts, including proximal and distal silastic segments, was done with a Large Field of View scintillation camera fitted with a high resolution collimator. The images were stored on and analysed with a Medical Data Systems A$^3$ computer (Medtronic, Ann Arbor, Mich.) interfaced with the scintillation camera. Dynamic image acquisition, 2 minute images (128×128 byte mode), was started simultaneously with the start of blood flow through the devices. A two minute image (128×128 byte mode) of a 3 ml autologous blood sample (collected in EDTA) was also acquired each time that the grafts were imaged to determine circulating blood radioactivity (blood standard). A region of interest of the graft segment was selected to determine the deposited and circulating radioactivity in each of the dynamic images. Radioactivity in a region of similar size of circulating radioactivity in the proximal segment of the extension tubing was determined, and subtracted from the radioactivity in the graft region to calculate deposited radioactivity. Platelet deposition was expressed as the total number of platelets deposited. The method to calculate this is described by Hanson et al, Arteriosclerosis (1985) 5:595-603.

Example 3—receptor binding measurements

6B4, its F(ab')$_2$ or Fab fragments were labelled with Na-$^{125}$I (Amersham, Buckinghamshire, UK) using the Iodogen method as described by Fraker et al., Biochem. Biophys. Res.Comm. (1978) 80:849-857. Iodogen was purchased from Pierce (Rockford, Ill.). Platelet-rich baboon plasma, adjusted with autologous plasma to a count of 100,000 platelets/µl, was incubated with different concentrations of iodinated 6B4, F(ab')2 or Fab fragments for 15 minutes at room temperature. The mixture was layered onto 20% sucrose buffer (wt/vol) containing 0.1% (wt/vol) bovine serum albumin (BSA) and centrifuged for 4 min at 10,000 g in Eppendorf tubes. The top fluid, including the plasma, was removed and the pellets were counted in a gamma-counter. This study was performed in duplicate on the platelet rich plasma of two baboons.

Example 4—In vitro and ex vivo platelet aggregation measurement

The aggregation of platelets in response to ristocetin (1.5 mg/ml final concentration; abp, N.Y.) was done on 10 ml blood collected in 1 ml of 3.2% trisodiumcitrate. Platelet rich plasma was prepared by differential centrifugation as described by Van Wyk et al, Thromb.Res. (1990) 57:601-9 and the platelet count adjusted to 200,000 platelets/µl with autologous plasma. The aggregation response was measured in a Monitor IV Plus aggregometer (Helena Laboratories, Beaumont, Tex.) and recorded for 5 minutes. The percent aggregation at 5 minutes was calculated as the difference in light transmission between platelet-rich and platelet-poor plasma.

In in vitro studies, the platelet rich plasma was preincubated for 5 minutes with serial dilutions of intact IgG 6B4, F(ab')2 or Fab fragments before aggregation was initiated. Inhibition of aggregation was calculated from the difference in the aggregation response of platelets without and with antibody or fragments. In the ex vivo determinations, inhibition was calculated from the difference in the aggregation response of platelets before and after treatment of the baboons.

Example 5—measurement of plasma concentrations of 6B4. F(ab')$_2$ or Fab fragments and of bleeding time.

Plasma concentrations were measured using a sandwich enzyme-linked immunoassay (ELISA). Briefly, microtiter plates were coated overnight at 4° C. with 5 µg/ml polyclonal goat anti-mouse IgG (Sigma). After blocking non-occupied binding sites with bovine serum albumin, serial dilutions of baboon plasma were added to the wells and incubated for two hours. Bound 6B4 (IgG, F(ab')$_2$ or Fab fragments) was detected by using goat anti-mouse IgG (Fab specific) conjugated to peroxidase (Sigma). Standard curves were constructed by adding known amounts of 6B4 (IgG, F(ab')$_2$ or Fab fragments) to baboon plasma.

Bleeding time was determined using the Simplate® II device (Organon Teknika,Durham, N.C.) according to the instructions of the manufacturer, the volar surface of the forearm of the baboons being shaved and a pressure cuff being applied and inflated to 40 mm Hg.

Example 6—In vitro effect of monoclonal antibody 6B4 and Fab fragments on binding of vWF to human GPIb under static and flow conditions Monoclonal antibody 6B4 binds to a (1-289) recombinant (r)GPIbβ fragment expressed by Chinese hamster ovary cells obtained from Meyer et al. *J. BioL Chem.* (1993) 268:20555-20562, indicating that its epitope is localized within the aminoterminal region of GPIbβ.

Monoclonal antibody 6B4 Fab fragments were further tested for inhibition of ristocetin- and botrocetin-induced binding of vWF to the rGPIbα fragment using an ELISA set-up, as described by Vanhoorelbeke et al. *Thromb. Haemost.* (2000):83:107-113. Microtiter plates were coated with 5 µg/ml monoclonal antibody 2D4 for 48 hours at 4° C. Monoclonal antibody 2D4, another anti-GPIb monoclonal antibody, binds to the rGPIbα fragment but does not block vWF binding. Non-adsorbed sites were blocked with 3% skimmed milk whereafter the plates were washed with tris buffered saline (hereinafter referred as TBS) containing 0.1% Tween 20 (TBS-Tw). Purified rGPIbα fragments were immobilised on monoclonal antibody 2D4 by incubating 2 µg/ml rGPIbα for 2 hours at 37° C. After washing with TBS-Tw, increasing concentrations of 6B4 Fab fragments (diluted in TBS-Tw) were added, followed by 1.25 or 0.6 µg/ml purified human vWF (available from the red Cross Belgium), respectively when ristocetin (300 µg/mL) or botrocetin (0.5 µg/mL) were used as modulators. Binding of vWF was determined by incubating for 1 hour with HRP conjugated polyclonal anti-vWF antibody (Dako, Glostrup, Denmark), diluted 1/3000 in TBS-Tw. The color reaction, stopped with 4 mol/l H$_2$SO$_4$ was generated with orthophenylenediamine (available from Sigma). The purification of botrocetin from crude *Bothrops jararaca* venom (available from Sigma) was performed according to Fujimura et al. *Biochemistry* (1991) 30:1957-1964.

The effect of 6B4 Fab fragments on shear-induced platelet adhesion to collagen was tested in a Sakariassen-type parallel-plate flow chamber at shear rates of 650, 1,300 and 2,600 sec$^{-1}$, according to Harsfalvi et al. *Blood* (1995) 85:705-7011. Human collagen type I (Sigma) was dissolved in 50 mM acetic acid (1 mg/ml), dialysed for 48 hours against PBS and subsequently sprayed onto plastic Thermanox coverslips and stored at room temperature overnight before use. 12 ml of blood, anticoagulated with LMW heparin (25 U/mL, Clexane, Rhône-Poulenc Rorer, France), was preincubated with 6B4 Fab fragments at 37° C. for 5 minutes and then used to perfuse the collagen-coated coverslips. After 5 minutes of perfusion, the platelets were fixed with methanol and the coverslips stained with May-Grunwald Giemsa. Platelet adhesion (percent of total surface covered with platelets) was evaluated with a light microscope connected to an image analyser. An average of 30 fields per coverslip were analysed. Platelet adhesion was expressed as % maximal platelet adhesion obtained in the absence of inhibitor.

Monoclonal antibody 6B4 Fab fragments block the ristocetin (1 mg/ml)-and botrocetin (0.5 µg/ml)-induced human platelet agglutination with an IC$_{50}$ of 1.2±0.3 µg/ml (24±6 nmol/l) and 2.0±0.5 µg/mL (40±10 nmol/l) respectively. 6B4 binds to an epitope localized on the aminoterminal part (His1-Val289) of GPIbα. As shown in FIG. 1, the 6B4 Fab fragments dose-dependently inhibited both the ristocetin- and botrocetin-induced binding of vWF to rGPIb, with an IC$_{50}$ of 1.8 µg/ml (36 nmol/l) and 2.5 µg/ml (50 nmol/l) respectively when the binding was induced by ristocetin (300 µg/ml) or botrocetin (0.5 µg/ml).

As shown in FIG. 2, the 6B4 Fab fragments inhibited platelet adhesion to collagen type I in a concentration-dependent manner at shear rates of 650, 1,300 and 2,600 sec$^{-1}$. A 50% reduction of surface coverage was obtained at a concentration of 3.5 µg/mL (70 nmol/l), 1.1 µg/mL (22 nmol/l) and 0.5 µg/mL (10 nmol/l) respectively for shear rates of 650, 1,300 and 2,600 sec$^{-1}$.

Example 7—in vivo studies in baboons: Dose response effect of 6B4 Fab-fragments on platelet adhesion and deposition Male baboons (*Papio ursinus*) weighing between 10 and 15 kg and being disease-free for at least 6 weeks were used according to procedures approved by the Ethics Committee for Animal Experimentation of the University of the Orange Free State (South Africa) and the National Code for Animal Use in Research, Education, Diagnosis and Testing of Drugs and Related Substances (South Africa). The baboons supported permanent Teflon®-Silastic Arteriovenous (AV) shunts implanted in the femoral vessels according to Hanson et al (cited supra). Blood flow through the shunts varied between 100 and 120 ml/min, resulting in wall shear rates between 800 and 1,000 sec$^{-1}$, which compares with the shear rates found in medium sized arteries. Handling of the baboons was achieved through anaesthesia with about 10 mg/kg ketamine hydrochloride (Anaket-V, Centaur Laboratory, South Africa).

In order to test the effect of the monoclonal antibody on platelet count, 6B4 and its F(ab')$_2$ and Fab fragments were administered to three different baboons. The injected dose was calculated to attain a plasma concentration of 1×KD$_{50}$ i.e. the concentration needed to occupy 50% of the receptors as determined in in vitro experiments.

Platelet-dependent arterial thrombus formation was induced by using bovine pericardium (0.6 cm$^2$) fixed in buffered gluteraldehyde according to the method disclosed by Quintero et al, *J.Heart Valve Dis.* (1998) 7:262-7. The pericardium was built into the wall of silicone rubber tubing (3 mm inside diameter). The method of preparation of the thrombogenic device is described by Kotze et al, *Thromb. Haemost.* (1993) 70:672-5, except that fixed bovine pericardium instead of Dacron® vascular graft material was used. In each experiment, a thrombogenic device, prefilled with saline to avoid a blood-air interface, was incorporated as an extension segment into the permanent AV-shunt by means of Teflon® connectors as previously disclosed by Hanson et al (cited supra).

In this first approach to determine the effect of 6B4 fragments on platelet adhesion, seven baboons were used and thirteen perfusion experiments were performed. In the first five experiments (3 baboons), a thrombogenic device was placed to determine deposition of platelets according to the method of example 2. After 30 minutes, the device was removed and blood flow through the permanent AV-shunt re-established. Fifteen minutes after removal of the device, each baboon was treated with a bolus of 80 µg/kg Fab fragments of 6B4 (in 2 ml saline) and again fifteen minutes later, a second thrombogenic device was placed for 30 minutes to determine the effect of the Fab fragments on thrombogenesis. The device was again removed and blood flow through the permanent shunt established. This was followed by a second bolus injection of Fab fragments (80 µg/kg) to attain a cumulative dose of 160 µg/kg. After fifteen minutes, a third thrombogenic device was placed for 30 minutes and platelet deposition measured according to the method of example 2. In four other experiments (2 baboons) the same study protocol was used but two doses of 320 µg/kg were administered.

In four other experiments (4 baboons), sham studies were performed by using the same protocol of placement of thrombogenic devices, but the baboons were not treated with Fab fragments.

Blood was collected at different periods of time (given in the figures) to determine platelet count and haematocrit (EDTA), circulating and platelet 5 associated radioactivity, the ex vivo aggregation of platelets in response to ristocetin (according to the method of example 4) and the plasma concentrations of Fab fragments (according to the method of example 5).

Example 8—in vivo studies in baboons—Effect of anti-GPIb 6B4 fragments on interplatelet cohesion In this second approach to determine the effect of 6B4 fragments on interplatelet cohesion, six baboons were selected in a manner similar to that of example 7 and used as follows. In all baboons, a thrombogenic device was placed for 24 minutes. In six experiments (3 baboons), the baboons received a bolus injection of Fab fragments of 110 µg/kg. The fragments were injected six minutes after placement of the thrombogenic device to allow enough platelets to be deposited to cover the collagen surface. In the six other experiments, the other three baboons did not receive Fab fragments.

As in example 7, blood was collected at different periods of time (given in the figures) to determine platelet count and haematocrit (EDTA), circulating 20 and platelet associated radioactivity, the ex vivo aggregation of platelets in response to ristocetin (according to the method of example 4) and the plasma concentrations of Fab fragments (according to the method of example 5).

EXPERIMENTAL RESULTS

Figure 3:
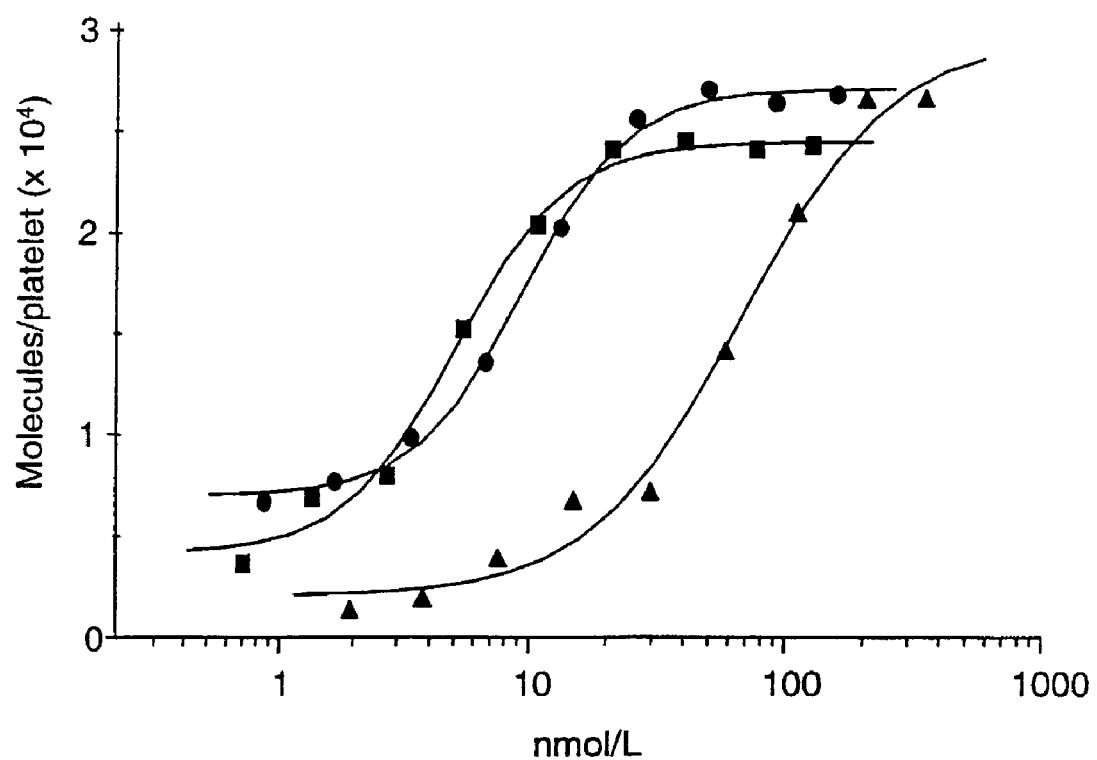
FIG. 3 shows binding curves of 6B4 and its fragments to baboon platelets in plasma.

FIG. 3 shows binding curves of anti-GPIb $^{125}$I-6B4 IgG (v),—F(ab')2 (λ) and—Fab fragments (σ) to baboon platelets in plasma. Binding of the antibody and its fragments to baboon platelets was dose-dependent and saturable: half saturation ($KD_{50}$) was obtained with 4.7 nmol/l, 6.4 nmol/l and 49.2 nmol/l for the monoclonal antibody 6B4 IgG, its F(ab')$_2$ and Fab fragments respectively.

Figure 4:
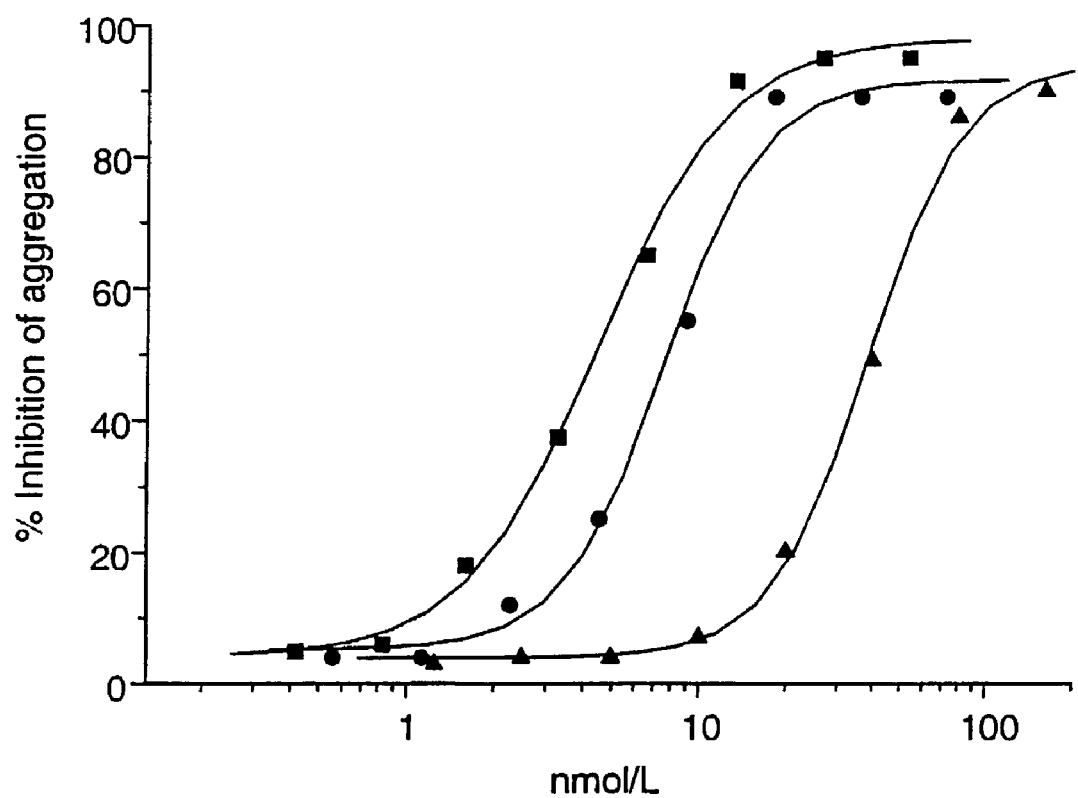
FIG. 4 shows the inhibitory effect of 6B4 and its fragments on ristocetin-induced baboon platelet aggregation.

FIG. 4 shows the inhibitory effect of anti-GPIb 6B4 IgG (v),—F(ab')2 (λ) and—Fab fragments (σ) on ristocetin-induced baboon platelet aggregation. When added at saturating concentrations, ristocetin-induced aggregation was completely abolished: $IC_{50}$-values were 4.5 nmol/l, 7.7 nmol/l and 40 nmol/l for the monoclonal antibody 6B4 IgG, its F(ab')$_2$ and Fab fragments respectively.

When considering the effect of injection of the monoclonal antibody 6B4, F(ab')$_2$ and Fab fragments on the peripheral platelet count in baboons, the dose of the 6B4 and its fragments used were calculated, for purposes of comparison to attain a plasma concentration of 1×$KD_{50}$. In one baboon, 100 µg/kg of intact antibody caused a profound decrease in the blood platelet count (<30×10$^9$ pl/l) within 10 minutes after injection. After 48 hours, the platelet count was still below 100×10$^9$ pl/l. When 6B4 F(ab')$_2$ fragments were injected into 2 baboons, the platelet count decreased rapidly to between 120 and 150×10$^9$ pl/, i.e. by approximately 60%, and then reached pre-infusion values within 24 hours. Finally when 80-320 µg/kg of the monovalent 6B4 Fab fragments was injected, the platelet count (45 min after injection) decreased only by approximately 10-20% and by 26% when 640 µg/kg was injected as shown in table 1 hereinafter.

FIG. 5 shows platelet deposition onto thrombogenic devices, containing bovine pericardium, placed consecutively at times 0 (λ), 60 (v) and 120 (σ) minutes for 30 minutes (top shaded bars) for panel A and following injection of 0 (λ), 80 (v) and 160 (σ), 320 (♦) and 640 (♥) µg/kg 6B4 Fab fragments for panel B. In the sham studies (FIG. 5A), placement of the previous graft had no significant effect on platelet deposition formed on subsequent grafts. In the treatment studies (FIG. 5B), dosages of 80 µg/kg and 160 µg/kg significantly inhibited platelet deposition in comparison to control, by approximately 43% and 53% respectively. Doses of 320 µg/kg and 640 µg/kg significantly reduced platelet deposition by 56% and 65% respectively.

Plasma levels of 6B4 Fab-fragments and inhibition of ex vivo agglutination determined on samples obtained 45 minutes or 2 hours after administration both changed dose- and time-dependently, as shown in table 1 hereinafter.

Bleeding times, determined in the treatment studies before and 45 minutes after injecting 80 to 320 µg/kg of 6B4 Fab fragments, were not significantly prolonged. Only a dose of 640 µg/kg significantly prolonged the bleeding time which was still less than doubled.

Figure 6:
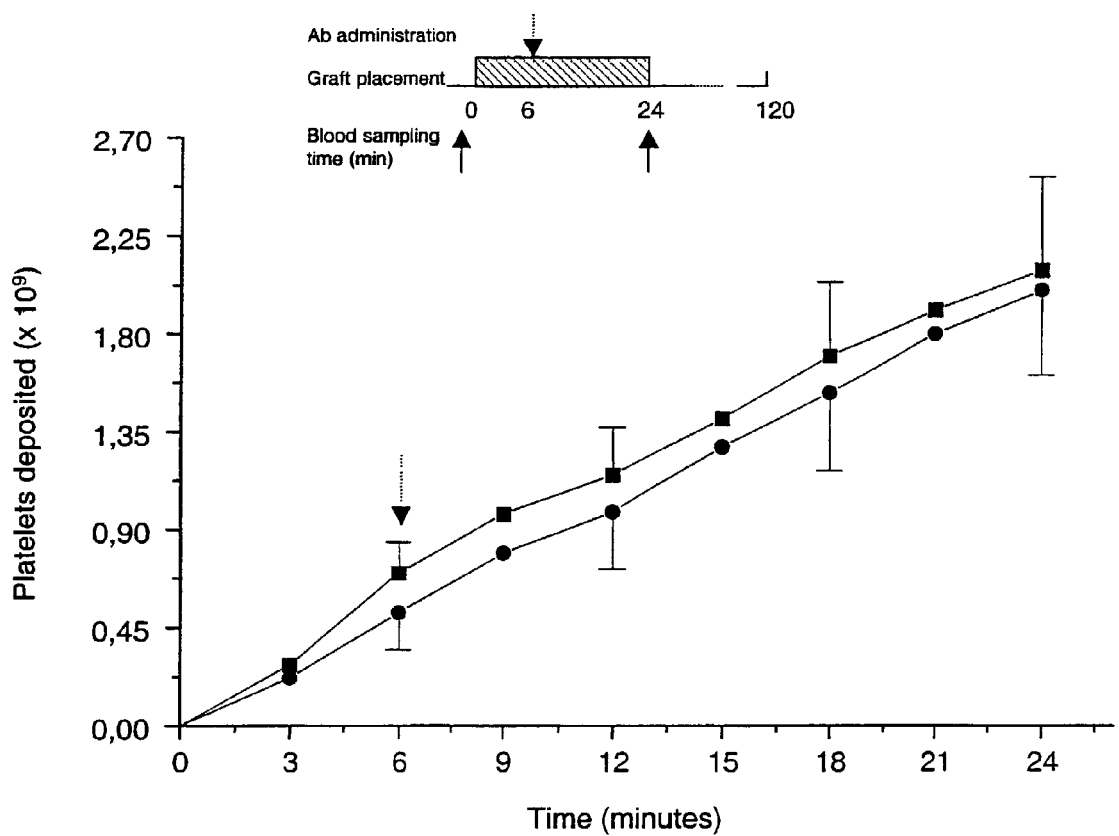
FIG. 6 shows the influence of late treatment of baboons with 6B4 Fab fragments on platelet deposition.

FIG. 6 shows the influence of late treatment of baboons with 6B4 Fab fragments on platelet deposition, the thrombogenic device being placed at time 0 and platelet deposition determined for 24 minutes (top shaded bar). After six minutes (arrow), baboons were either untreated (v) or treated with a bolus of 110 (λ) µg/kg 6B4 Fab fragments. It is thus shown that 110 µg/kg 6B4 Fab fragment did not affect platelet deposition when injected after a thrombus was allowed to form for an initial 6 minutes.

INTERPRETATION OF EXPERIMENTAL RESULTS

The anti-GPIb monoclonal antibody 6B4, its F(ab')$_2$ and Fab fragments potently inhibited the binding of vWF to a recombinant GPIbα fragment (His1-Val289) and dose-dependently inhibited vWF-dependent human platelet agglutination. The intact monoclonal antibody and its fragments also dose-dependently inhibited human platelet adhesion to type I collagen in a flow chamber at wall shear rates of 650, 1300 and 2600 sec$^{-1}$. This inhibition was shear-dependent, i.e. more pronounced at higher shear.

6B4, its F(ab')$_2$ and Fab fragments also bind to and inhibit baboon platelets and inhibit baboon platelets with much the same characteristics as human platelets. As a result baboons were used for in vivo and ex vivo studies. An almost immediate, profound and irreversible thrombocytopenia developed when the intact antibody was injected into a baboon, similar to what was observed when other anti-GPIb monoclonal antibodies were injected into different experimental animals. The F(ab')$_2$ fractions also caused immediate, but reversible thrombocytopenia, but to a lesser extent than the intact antibody. The Fab fractions, on the other hand, had only a moderate effect on the blood platelet count, which strongly suggests that the Fc portion of the monoclonal antibody plays a part in the development of the irreversible thrombocytopenia.

The 6B4 Fab fractions were used to assess an antithrombotic effect in a baboon model of arterial thrombosis. The gluteraldehyde fixed bovine pericardium was highly thrombogenic: after 30 minutes of exposure to native flowing blood, approximately 3×10$^9$ platelets deposited on the area of 0.6 cm$^2$. In similar studies, only approximately 0.7×10$^9$ platelets accumulated on Dacron vascular graft material (0.9 cm$^2$) according to Kotzé et al., *Thromb. Haemost* (1993) 70:672-675. It is therefore not surprising that a number of control thrombogenic devices occluded before 30 minutes of exposure to flowing blood.

Treatment of baboons with 6B4 Fab fragments inhibited platelet deposition on the thrombogenic devices by between 43 and 65%. The observed effect must be ascribed to the monoclonal antibody, since sequential placement of thrombogenic devices in untreated baboons caused no decreased deposition. No complete inhibition of platelet deposition was observed, even at high doses.

Example 9—in vivo studies in baboons: effect of 6B4 Fab fragments on cyclic flow variations in stenosed. endothelium-injured arteries The experimental model used herein is adapted from the model originally described by J.D.Folts et al. in *Circulation* (1982) 65:248-255 as a canine model of coronary artery stenosis with intimal damage. Basically, this model allows to study the cyclic flow reductions in coronary blood flow due to platelet-dependent thrombi forming at the site of a coronary stenosis which was created by the placement of a fixed constrictor. It provides a reproducible pattern of recurrent thrombosis to be established and is widely accepted as very effective and clinically relevant in testing potential antithrombotic agents. Our adaptation is such that the model was set-up in one femoral artery of the baboons, since the 6B4 Fab fragments do not cross react with canine platelets.

A. Surgical preparation and study protocol

Normal baboons (*Papio ursinus*) weighing 10-15 kg, disease-free for at least six weeks before the experiments, were used. All experiments were approved by the Ethics Committee for Animal Experimentation of the University of the Free State in accordance with the National Code for Animal Use in Research, Education, Diagnosis and Testing of Drugs and Related Substances in South Africa. Baboons were anaesthetized with ketamine hydrochloride (≈10 mg/kg IM; Anaket-V, Centaur Laboratory). The intra-arterial pressure was continuously monitored throughout the procedure. Blood for the laboratory tests (examples 3-5) was obtained from one of the femoral veins.

First, a calibrated electromagnetic flow probe was placed around the proximal portion of the isolated femoral artery of the baboons in order to measure arterial blood flow. After the animal was allowed to stabilize for approximately 30 minutes, the endothelium of the femoral artery was injured by gently squeezing with forceps, and cyclic flow reductions due to platelet-dependent thrombus formation were induced by placement of a constrictor. When flow declined to near zero, blood flow through the constricted femoral artery was restored by manually shaking the constrictor. The cyclic pattern of decreasing arterial blood flow following restoration was referred to cyclic flow reductions, and this pattern was continuously monitored for 60 minutes.

The baboons in which the cyclic flow reductions were studied, were divided into three groups. One group (2 baboons) received a placebo (saline solution), the second group (4 baboons) was treated with a bolus injection of 600 µg/kg 6B4 Fab fragments and the third group (3 baboons) received an injection of 2 mg/kg 6B4 Fab fragments. In addition, 4 mg/kg 6B4 Fab fragments were injected in one baboon in order to determine the effect of such high dose on platelet count, receptor occupation, bleeding time and platelet aggregation but cyclic flow reductions were not followed in this baboon.

Animals instrumented to produce cyclic flow reductions were treated with 6B4 Fab fragments or placebo after a 30 minutes baseline monitoring period. Cyclic flow reductions were continuously monitored in each animal during 60 minutes. The anti-thrombotic effect was quantified by comparing the frequency of cyclic flow reductions per hour before and after drug administration. Blood samples for the different laboratory measurements (platelet count, haematocrit, platelet aggregation, receptor occupation and plasma levels) were drawn at several periods in time: before the 60 minutes monitoring period and respectively 30, 60, 150, 300 minutes and 24 hours after treatment.

B. Results

B.1. effect of 6B4 Fab fragments on cyclic flow reductions (FIG. 7)

In the baboons that received a placebo injection of saline solution, the frequency of the cyclic flow reductions (CFR) at 60 minutes after injection was not changed (107±7%) significantly as compared to the pre-treatment control period. A dose of 600 µg/kg 6B4 Fab fragments resulted in a partial inhibition of the cyclic flow reductions, reducing their frequency to 41±15%. A dose of 2 mg/kg completely abolished the cyclic flow reductions in all three animals studied and this inhibition (6±6%) was observed throughout the 60 minutes study period. Heart rate, blood pressure and haematocrit remained unchanged during the study.

B.2. effect of 6B4 Fab fragments on platelet count and bleeding times (FIGS. 8 and 9)

The platelet count (FIG. 8) was not significantly affected by injection of 600 µg/kg, 2 mg/kg or 4 mg/kg of the 6B4 Fab fragments. Also the bleeding time (FIG. 9) was not significantly prolonged by injection of 600 µg/kg, 2 mg/kg or 4 mg/kg of the 6B4 Fab fragments.

B.3. Inhibition of ex vivo platelet aggregation (FIG. 10)

6B4 Fab fragments inhibited the ex vivo ristocetin-induced platelet aggregation in a dose- and time-dependent manner when administered to the baboons (FIG. 10). Aggregation was totally abolished 30 minutes after injection and, as compared to the aggregation response before injection, aggregation was significantly (p<0.05) reduced to 16.8%, 5.2% and 2% 60 minutes and to 68.8% (p>0.05), 19.2% and 16% 150 minutes after a bolus injection of 600 µg/kg, 2 and 4 mg/kg 6B4 Fab fragments respectively. The inhibitory effect lasted for about 150 minutes and returned to normal values within 24 hours.

B.4. Receptor occupancy (FIG. 11)

Figure 11:
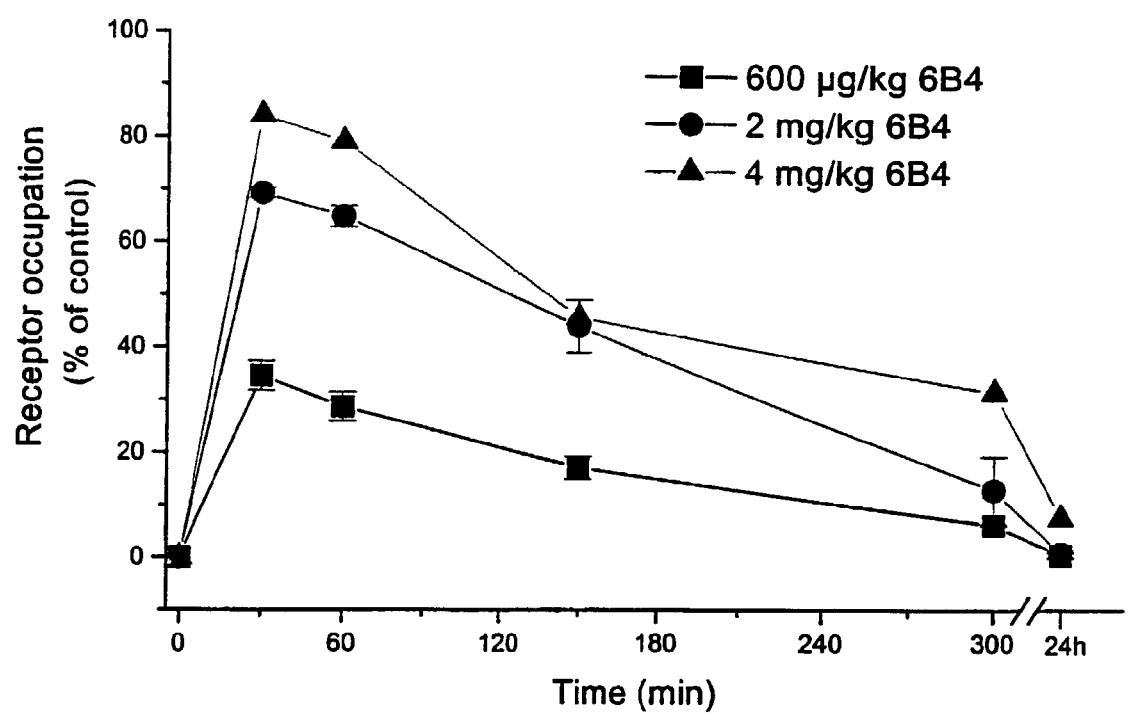
FIG. 11 shows the occupancy of GPIb receptors by 6B4 Fab fragments.

The occupancy of GPIb receptors by the 6B4 Fab fragments is shown in FIG. 11. Thirty minutes following a bolus injection of 600 µg/kg, 2 and 4 mg/kg 6B4 Fab fragments, approximately 34.5%, 69.3% and 84% of the GPIb receptors were occupied respectively. The receptor occupancy was 28.6%, 64.8% and 79% after 60 minutes; 17.1%, 43.9% and 45.6% after 150 minutes and dropped to 6.3%, 12.9% and 31.3% after 300 minutes following injection of respectively 600 µg/kg, 2 and 4 mg/kg 6B4 Fab fragments. The decrease in receptor occupancy corresponds with the time course of the ex vivo ristocetin-induced aggregation results.

C. Interpretation of experimental results

It is well established that platelet adhesion, activation and aggregation plays a pivotal role in the development of coronary artery syndromes. In particular, the high shear stress present in the constricted coronary arteries is an important initiator of the platelet activation and aggregation. Several investigators have shown that cyclic flow reductions in stenosed damaged canine coronary arteries can be prevented by metabolic inhibition of platelet activation, or by blockade of the GPIIb/IIIa receptor.

In this study we have shown that administration of Fab fragments of the inhibitory anti-GPIb monoclonal antibody 6B4 is effective in diminishing or abolishing cyclic flow variations in stenosed, endothelium-injured femoral arteries in non-human primates. The presumed mechanism by which this occurs is the inhibition of the interaction of the platelet glycoprotein Ib receptor and the vessel wall-bound von Willebrand factor. This prevents platelet activation and aggregation as well as the release of pro-aggregatory and vasoconstrictor substances responsible for these cyclic flow variations.

6B4 Fab fragments completely abolished the cyclic flow reductions at a dose of 2 mg/kg, and reduced them by 59% after injection of 600 μg/kg. Bleeding times were not significantly prolonged, even when injecting 4 mg/kg of the 6B4 fragments, suggesting that 6B4 Fab fragments are a useful anti-thrombotic agent with low bleeding risk. Moreover, there was no fall in platelet count, again indicating that injection of the 6B4 fragments is not expected to cause any haemostatic problems. In vivo administration of the 6B4 Fab fragments resulted in a dose- and time-dependent inhibition of ex vivo ristocetin-induced platelet aggregation and correlated with the receptor occupancy. The duration of the effects of the 6B4 Fab fragments persisted for about 3 hours when a dose that completely abolished the cyclic flow reductions (>2 mg/kg 6B4 Fab fragments) was given, with receptor occupancy and anti-platelet effects (ristocetin-aggregation) returning to baseline values about 6 hours after injection. In conclusion 6B4 Fab fragments demonstrate the desired properties to be promising compounds for the treatment of acute coronary syndromes with a low bleeding risk.

Example 10—cloning and sequencing of monoclonal antibody 6B4

In order to reduce the possible immunogenicity of the murine anti-GPIb monoclonal antibody 6B4, it may be necessary to construct chimeric antibodies combining the variable region of the mouse antibody with a human antibody constant region. Depending on the antibody, such chimeric antibodies have been found from substantially reducing to little affecting the immunogenic response. Further humanisation by complementary determining region-grafting or re-surfacing usually has proven to be a successful approach. In order to produce such humanised antibodies, a first step is to determine the sequence of the murine antibody.

Cloning of variable region cDNAs

Total RNA from approximately 3×10$^7$ 6B4-hybridoma cells grown in 75 mL T-flasks was prepared using the Qiagen RNeasy Midi Procedure (Westburg) following the manufacturers' instructions and next quantitated by an OD260 reading. cDNA was synthesized from the total RNA by incubating 2 μg of tRNA with 1 μM of poly(dT)$_{15}$ adaptor primer and 4 U of Omniscript reverse transcriptase in a total volume of 20 μl with other reaction buffers and following incubation times as recommended by the manufacturer (Qiagen Omniscript RT Kit) (Westburg).

Next, the V genes were amplified for cloning into the pCRII-TOPO® vector (TOPO TA-Cloning® Kit, In Vitrogen) for sequence determination. Polymerase chain reaction amplification was done using $V_H$back (5'-CAGGTSM-ARCTGCAGSAGTCWGG-3') [SEQ ID NO:5] and $V_H$for (5'-TGAGGAGACGGTGACCGTGGTCCCTTG-GCCCCAG-3') [SEQ ID NO:6], $V_L$back (5'-GACAT-TGAGCTCACCCAGTCTCCA-3') [SEQ ID NO:7] and $V_{K2}$for (5'-GGAAGCTTGAAGATGGATACAGTTGGTG-CAGC-3') [SEQ ID NO:8] primers with M, R, W and S respectively (A/C), (A/G), (A/T) and (C/T) (all from Eurogentec, Herstal, Belgium) and $V_H$back, $V_H$for and $V_L$back are complementary to the 5'-terminal part of the framework region FR-1 and to the 3'-terminal part of the FR-4 of the $V_H$- and $V_L$-genes respectively and $V_{K2}$ for anneals to the $C_K$ sequence. Polymerase chain reactions were performed in a programmable heating block using 30 rounds of temperature cycling (92° C. for 1 minute, 55° C. for 1 minute and 72° C. for 1 minute). The reactions included the cDNA, 1 μg of each primer and 2.5 U of Hotgold polymerase (Eurogentec) in final volume of 50 μl, with the reaction buffers as recommended by the manufacturer (Vitrogen). The polymerase chain reaction product bands were analyzed on a 1.5% agarose gel.

Transformation was done using the heat-shock method and using *E. coli*-TOP-10 cells (TOPO TA-Cloning™ Kit, In Vitrogen) according to the manufacturers' instructions. The cells from each transformation were plated onto LB+ampicillin). Transformation was checked by polymerase chain reaction amplification of the inserts and next analyzed on a 1.5% agarose gel. Positive clones were grown up for purification of plasmid DNA by the Qiagen Maxi plasmid purification kit.

Sequencing reactions were performed with the ABI Prism Big Dye terminator cycle Sequencing Ready Reaction kit (Perkin Elmer Applied Biosystems, Netherlands) according to the manufacturer's instructions using M13 Forward primer 5'-TTCCTCGACGCTAACCTG-3' and M13 Reverse primer 5'-GATTTAATCTGTATCAGG-3' and which align to the pCRII-TOPO™ vector.

RESULTS AND INTERPRETATIONS

The cDNA from the heavy-chain variable domain genes were amplified by polymerase chain reaction using primers that hybridize to the framework regions FR-1 and FR-4. For amplification of the light-chain variable domain genes we used a primer that hybridizes to FR-1 and one that anneals in the constant region. These $V_H$ and $V_L$ genes were next cloned into the PCRII-TOPO™ vector and transformed into *E. coli* TOP10 cells. By using appropriate primers the $V_H$ and $V_L$ genes were next sequenced. The translated amino acid sequences are given in FIGS. 12 (light chains) and 13 (heavy chains) respectively, and the six complementary determining regions conferring epitope specificity are indicated in these figures. The heavy chain ($V_H$) revealed a sequence closely related to mouse heavy chain subgroup Ib, whereas the light chain ($V_L$) gene sequence matches to mouse K-chain subgroup V. Given our choice of priming sites, it is not possible to determine the exact sequence at both ends of the V genes, as it is dictated by the primer (amino acid residues 1-8 of FR1 of the $V_L$ and residues 1-8 of FR1 of the $V_H$ and 111-121 of FR4 of the $V_H$). Nevertheless, these uncertainties in the framework regions are unlikely to affect antigen specificity since this is determined by the complementary determining regions.

TABLE 1

Platelet counts, plasma levels of 6B4 Fab-fragments, ex vivo ristocetin-induced platelet agglutination and bleeding times following administration of 80-640 µg/kg 6B4 Fab fragments to baboons. Values are given as mean ± SE. Statistical comparisons were made using student t-test for paired sample groups (*p < 0.05).

| Dose (µg/kg) | n | Time (min) | Platelet counts (×10³/µL) | (% decrease) | Plasma levels (µg/mL) | % Inhibition of ex vivo ristocentin-induced (1.5 mg/mL) platelet agglutination | Bleeding times (sec) |
|---|---|---|---|---|---|---|---|
| 0 | 5 | Pre | 307 ± 32 | (0) | 0.07 ± 0.03 | 0 | 190 ± 20 |
| 80 | 5 | 90 | 272 ± 22 | (11) | 1.72 ± 0.14 | 26 ± 9 | 160 ± 33 |
| 160 | 5 | 150 | 248 ± 19 | (19) | 4.84 ± 0.56 | 47 ± 12* | 250 ± 45 |
|  |  | 270 | 315 ± 31 |  | 0.45 ± 0.09 | 8 ± 3 | ND |
| 0 | 4 | Pre | 283 ± 23 | (0) | 0.02 ± 0.01 | 0 | 232 ± 42 |
| 320 | 4 | 90 | 219 ± 10 | (23) | 9.13 ± 0.48 | 25 ± 21 | 340 ± 63 |
| 640 | 4 | 150 | 210 ± 13 | (26) | 15.35 ± 1.38 | 80 ± 9* | 405 ± 45* |
|  |  | 270 | 238 ± 20 | (16) | 1.19 ± 0.09 | 15 ± 9 | ND |
|  |  | 24 h | 236 ± 13 | (17) | 0.04 ± 0.01 | 7 ± 3 | ND |

ND non determined

The invention claimed is:

1. A pharmaceutical composition comprising a monovalent antibody fragment, which prevents the binding of von Willebrand factor (vWF) to human platelet glycoprotein Ib (GPIb) and binds in vivo to human platelet GPIb without incurring thrombocytopenia, and a pharmaceutically acceptable carrier, wherein the variable region of said fragment comprises SEQ ID NO:4

2. A pharmaceutical composition comprising a monovalent antibody fragment, which prevents the binding of von Willebrand factor (vWF) to human platelet glycoprotein Ib (GPIb) and binds in vivo to human platelet GPIb without incurring thrombocytopenia, and a pharmaceutically acceptable carrier, wherein said monovalent antibody fragment is obtained from a monoclonal antibody produced by the cell line deposited with the Belgian Coordinated Collections of Microorganisms, under accession number LMBP 5108CB.

3. A monoclonal antibody produced by the cell line deposited with the Belgian Coordinated Collections of Microorganisms, under accession number LMBP 5108CB.

4. A cell line, capable of producing an antibody directed against GPIb deposited with the Belgian Coordinated Collections of Microorganisms, under accession number LMBP 5108CB.

5. A humanized antibody fragment derivable from the monoclonal antibody of claim 3, wherein said humanized antibody fragment binds GPIb.

6. A monovalent antibody fragment which binds in vivo to human platelet GPIb and prevents the binding of von Willebrand factor to human platelet GPIb, wherein said monovalent antibody fragment is obtained from a monoclonal antibody produced by the cell line deposited with the Belgian Coordinated Collections of Microorganisms under accession number LMBP 5108CB.

7. A monovalent antibody fragment which binds in vivo to human platelet GPIb and prevents the binding of von Willebrand factor to human platelet GPIb, wherein said monovalent antibody fragment includes a variable region comprising SEQ ID NO:4.

* * * * *

UNITED STATES PATENT AND TRADEMARK OFFICE
CERTIFICATE OF CORRECTION

| | |
|---|---|
| PATENT NO. | : 7,332,162 B1 |
| APPLICATION NO. | : 10/049868 |
| DATED | : February 19, 2008 |
| INVENTOR(S) | : Deckmyn et al. |

It is certified that error appears in the above-identified patent and that said Letters Patent is hereby corrected as shown below:

Title Page, in (87) PCT Pub. Date, replace "Aug. 8, 2000" with --Feb. 15, 2001--;

Title Page, under OTHER PUBLICATIONS, in Cowenberghs, replace "Arteriosclerosis, Thrombosis abd Vascular Biology" with --Arteriosclerosis, Thrombosis and Vascular Biology--;

In Schultz, replace "Coardiovascular" with --Cardiovascular--;

In Gold, replace "PharmacodynamicStudy" with --Pharmacodynamic Study--;

In Miller JL et al, replace "blood" with --*Blood*--.

Column 2, Line 13, replace "forrn" with --form--.

Column 3, Line 35, replace "letal" with --lethal--.

Column 4, Line 15, replace "cmss" with --cross--;

Line 31, replace "anti-thrombotc" with --anti-thrombotic--;

Line 39, replace "thrombocytopenia, A third" with --thrombocytopenia. A third--.

Column 5, Line 48, replace "occuring" with --occurring--.

Column 7, Line 55, replace "succesful" with --successful--.

Column 8, Line 3, replace "5108CB. which" with --5108CB, which--;

Line 53, replace "injectionable" with --injectable--.

Signed and Sealed this
Twentieth Day of November, 2012

David J. Kappos
*Director of the United States Patent and Trademark Office*

CERTIFICATE OF CORRECTION (continued)
U.S. Pat. No. 7,332,162 B1

Column 9, Line 41, replace "moI/I" with --mol/l--;

Line 53, replace "mmoI/I" with --mmol/l--;

Line 57, replace "mmoI/I" with --mmol/l--.

Column 10, Line 31, replace "lodogen method" with --Iodogen method--;

Line 32, replace "lodogen" with --Iodogen--.

Column 13, Line 47, replace "circulating 20 and platelet" with --circulating and platelet--.

Column 15, Line 40, replace "pattem" with --pattern--.

SEQUENCE LISTING

<160> NUMBER OF SEQ ID NOS: 10

<210> SEQ ID NO 1
<211> LENGTH: 359
<212> TYPE: DNA
<213> ORGANISM: Mus musculus
<220> FEATURE:
<221> NAME/KEY: V_region
<222> LOCATION: (1)...(359)
<220> FEATURE:
<221> NAME/KEY: primer_bind
<222> LOCATION: (1)...(24)
<223> OTHER INFORMATION: Vkback primer
<220> FEATURE:
<221> NAME/KEY: misc_feature
<222> LOCATION: (70)...(100)
<223> OTHER INFORMATION: complementary determining region one
<220> FEATURE:
<221> NAME/KEY: misc_feature
<222> LOCATION: (144)...(165)
<223> OTHER INFORMATION: complementary determining region two
<220> FEATURE:
<221> NAME/KEY: misc_feature
<222> LOCATION: (262)...(289)
<223> OTHER INFORMATION: complementary determining region three
<220> FEATURE:
<221> NAME/KEY: primer_bind
<222> LOCATION: (328)...(359)
<223> OTHER INFORMATION: Vk2for primer

<400> SEQUENCE: 1

```
gacattgagc tcacccagtc tccagcaatc atgtctgcat ctccagggga gaaggtcacc      60
atgacctgca gtgccagttc aagtgttaat tacatgcact ggttccagca ggagtcgggc     120
accttcccca aaagaaggat ttatgacaca tccaaactgg cttctggagt ccctgctcgc     180
ctcagtggca gtgggtctgg gacagaattc accctggaaa tcagtagagt gaaggctgag     240
gatgtgggtg tgtattactg tcaacaactt gtagagtatc cgctcacgtt cggtgctggg     300
accaagctgg agctgaaacg ggctgatgct gcaccaactg tatccatctt caagcttcc      359
```

<210> SEQ ID NO 2
<211> LENGTH: 363
<212> TYPE: DNA
<213> ORGANISM: Mus musculus
<220> FEATURE:
<221> NAME/KEY: V_region

```
<222> LOCATION: (1)...(363)
<220> FEATURE:
<221> NAME/KEY: primer_bind
<222> LOCATION: (1)...(24)
<223> OTHER INFORMATION: Vhback primer
<220> FEATURE:
<221> NAME/KEY: misc_feature
<222> LOCATION: (90)...(105)
<223> OTHER INFORMATION: complementary determining region one
<220> FEATURE:
<221> NAME/KEY: misc_feature
<222> LOCATION: (147)...(195)
<223> OTHER INFORMATION: complementary determining region two
<220> FEATURE:
<221> NAME/KEY: misc_feature
<222> LOCATION: (291)...(330)
<223> OTHER INFORMATION: complementary determining region three
<220> FEATURE:
<221> NAME/KEY: primer_bind
<222> LOCATION: (330)...(360)
<223> OTHER INFORMATION: Vhfor primer

<400> SEQUENCE: 2
caggtgcagc tgcaggagtc tggacctggc ctggtggcgc cctcacagag cctgtccatc      60
acttgcactg tctctgggat ttcattaaac agatatggtg tacactgggt tcgccagcct     120
ccaggaaagg gtctggagtg gctgggagta atatggactg gtggaagcac aaattataat     180
tcggctctca gtccagact gagcatcagc aaagacaact ccaagagcca agttttctta      240
aaaatgaaca gtctgcagac tgatgacaca gccatgtact actgtgccag agatcgatct     300
actatgatta cggcctatgc tatggactac tggggccaag gaccacggt caccgtctcc      360 tca                                                                    363

<210> SEQ ID NO 3
<211> LENGTH: 119
<212> TYPE: PRT
<213> ORGANISM: Mus musculus

<400> SEQUENCE: 3

Asp Ile Glu Leu Thr Gln Ser Pro Ala Ile Met Ser Ala Ser Pro Gly
 1               5                  10                  15

Glu Lys Val Thr Met Thr Cys Ser Ala Ser Ser Ser Val Asn Tyr Met
            20                  25                  30

His Trp Phe Gln Gln Glu Ser Gly Thr Phe Pro Lys Arg Arg Ile Tyr
        35                  40                  45

Asp Thr Ser Lys Leu Ala Ser Gly Val Pro Ala Arg Leu Ser Gly Ser
    50                  55                  60

Gly Ser Gly Thr Glu Phe Thr Leu Glu Ile Ser Arg Val Lys Ala Glu
65                  70                  75                  80

Asp Val Gly Val Tyr Tyr Cys Gln Gln Leu Val Glu Tyr Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Lys Leu
        115

<210> SEQ ID NO 4
<211> LENGTH: 121
<212> TYPE: PRT
<213> ORGANISM: Mus musculus

<400> SEQUENCE: 4

Gln Val Gln Leu Gln Glu Ser Gly Pro Gly Leu Val Ala Pro Ser Gln
```

```
  1               5                  10                 15
Ser Leu Ser Ile Thr Cys Thr Val Ser Gly Ile Ser Leu Asn Arg Tyr
                20                 25                 30

Gly Val His Trp Val Arg Gln Pro Pro Gly Lys Gly Leu Glu Trp Leu
                35                 40                 45

Gly Val Ile Trp Thr Gly Gly Ser Thr Asn Tyr Asn Ser Ala Leu Met
                50                 55                 60

Ser Arg Leu Ser Ile Ser Lys Asp Asn Ser Lys Ser Gln Val Phe Leu
65                  70                 75                 80

Lys Met Asn Ser Leu Gln Thr Asp Asp Thr Ala Met Tyr Tyr Cys Ala
                85                 90                 95

Arg Asp Arg Ser Thr Met Ile Thr Ala Tyr Ala Met Asp Tyr Trp Gly
                100                105                110

Gln Gly Thr Thr Val Thr Val Ser Ser
                115                120
```

<210> SEQ ID NO 5
<211> LENGTH: 23
<212> TYPE: DNA
<213> ORGANISM: Mus musculus

<400> SEQUENCE: 5
caggtsmarc tgcagsagtc wgg                                        23

<210> SEQ ID NO 6
<211> LENGTH: 34
<212> TYPE: DNA
<213> ORGANISM: Mus musculus

<400> SEQUENCE: 6
tgaggagacg gtgaccgtgg tcccttggcc ccag                            34

<210> SEQ ID NO 7
<211> LENGTH: 24
<212> TYPE: DNA
<213> ORGANISM: Mus musculus

<400> SEQUENCE: 7
gacattgagc tcacccagtc tcca                                       24

<210> SEQ ID NO 8
<211> LENGTH: 32
<212> TYPE: DNA
<213> ORGANISM: Mus musculus

<400> SEQUENCE: 8
ggaagcttga agatggatac agttggtgca gc                              32

<210> SEQ ID NO 9
<211> LENGTH: 18
<212> TYPE: DNA
<213> ORGANISM: Mus musculus

<400> SEQUENCE: 9
ttcctcgacg ctaacctg                                              18

<210> SEQ ID NO 10
<211> LENGTH: 18
<212> TYPE: DNA
<213> ORGANISM: Mus musculus

```
<400> SEQUENCE: 10
gatttaatct gtatcagg                                                        18
```